(12) United States Patent
Luyten et al.

(10) Patent No.: US 7,863,045 B2
(45) Date of Patent: Jan. 4, 2011

(54) ISOLATION OF SKELETAL PRECURSOR CELLS

(75) Inventors: Frank Luyten, Kraainem (BE); Cosimo De Bari, Aberdeen (GB); Francesco Dell'Accio, Bromley (GB)

(73) Assignee: Tigenix N.V., Leuven (BE)

( * ) Notice: Subject to any disclaimer, the term of this patent is extended or adjusted under 35 U.S.C. 154(b) by 163 days.

(21) Appl. No.: 12/176,256

(22) Filed: Jul. 18, 2008

(65) Prior Publication Data
US 2009/0123927 A1    May 14, 2009

Related U.S. Application Data

(62) Division of application No. 10/089,994, filed as application No. PCT/BE00/00120 on Oct. 6, 2000, now abandoned.

(30) Foreign Application Priority Data

Oct. 6, 1999  (EP) ................................. 99203274
Oct. 7, 1999  (EP) ................................. 99203290

(51) Int. Cl.
C12N 5/00 (2006.01)
C12N 5/02 (2006.01)
C12N 5/071 (2006.01)
G01N 33/567 (2006.01)

(52) U.S. Cl. .................. 435/378; 435/7.21; 435/366; 435/372

(58) Field of Classification Search .............. 435/378, 435/7.21, 366, 372
See application file for complete search history.

(56) References Cited

U.S. PATENT DOCUMENTS

| | | |
|---|---|---|
| 5,197,985 A | 3/1993 | Caplan et al. |
| 5,226,914 A | 7/1993 | Caplan et al. |
| 5,486,359 A | 1/1996 | Caplan et al. |
| 5,648,219 A | 7/1997 | MacKay et al. |
| 5,683,906 A | 11/1997 | Moore |
| 5,733,542 A | 3/1998 | Haynesworth et al. |
| 5,811,094 A | 9/1998 | Laplan |
| 5,830,682 A | 11/1998 | Moore |
| 5,837,539 A | 11/1998 | Caplan et al. |
| 5,919,702 A | 7/1999 | Purchio et al. |
| 5,972,703 A | 10/1999 | Long |
| 6,010,696 A | 1/2000 | Caplan et al. |
| 6,087,113 A | 7/2000 | Caplan et al. |

FOREIGN PATENT DOCUMENTS

| | | |
|---|---|---|
| WO | WO 99/28443 | 6/1990 |
| WO | WO 96/07733 | 3/1996 |
| WO | WO 96/41620 | 12/1996 |
| WO | WO 97/07200 | 2/1997 |
| WO | WO 97/26326 | 7/1997 |
| WO | WO 98/17791 | 4/1998 |
| WO | WO 98/35022 | 8/1998 |
| WO | WO 98/59035 | 12/1998 |

OTHER PUBLICATIONS

Thomson et al. PNAS, 92:7844-7848 (Aug. 1995).*
NIH. Stem Cells: Scientific Progress and Future Research Directions, Department of Health and Human Services, Chapter 1, pp. 1-4, Jun. 2001.*
Chang et al., "Cartilage-derived Morphogenetic Proteins: New Members of the Transforming Growth Factor β Superfamily Predominately Expressed in Long Bones During Human Embryonic Development," *J. Bio. Chem.* 45:28277-28234 (1994).
Erlacher et al., "Cartilage—Derived Morphogenetic Proteins and Osteogenic Protein-1 Differentially Regulate Osteogenesis", *Journal of Bone and Mineral Research*, 13(3): 383-392 (1998).
Erlacher et al., "Presence of Cartilage-derived Morphogenetic Proteins in Articular Cartilage and Enhancement of Matrix Replacement In Vitro," *Arthritis & Rheumatism*, 41(2): 263-273 (1998).
*Guidelines for Human Embryonic Stem Cell Research*, pp. 116 and 119, Washington, DC: Natl. Academies Press, 2005.
Hui et al., "Mesenchymal Stem Cells in Musculoskeletal Tissue Engineering: A Review of Recent Advances in National University of Singapore," *Ann. Acad. Med. Singapore*, 34:206-212 (2005).
Kyoizumi et al., "Implantation and Maintenance of Functional Human Bone Marrow in *SCID*-hu Mice," *Blood*, 79(7):1704-1711 (1992).
Luyten et al., "Cartilage-derived Morphogenetic Protein-1," *Int. J. Biochem. Cell Bio.* 29:1241-1244 (1997).
Nevo, "The Manipulated Mesenchymal Stem Cells in Regenerated Skeletal Tissues," *Cell Transplantation* 7(1): 63-70 (1998).
Nifuji et al., "Coordinated Expression of Noggin and Bone Morphogenetic Proteins (BMPs) During Early Skeletogenesis and Induction of Noggin Expression by BMP-7," 14(12): 2057-2066 (1999).
Takahashi at al., "Osteoclast-like Cells Form in Long-term Human Bone Marrow but not in Peripheral Blood Cultures," *J. Clin. Invest.* 83:543-550 (1989).
Examiner's Report for Canadian Application No. 2,386,506, dated Jul. 9, 2010.

* cited by examiner

*Primary Examiner*—Thaian N Ton
(74) *Attorney, Agent, or Firm*—Clark & Elbing LLP

(57) ABSTRACT

Cartilage-derived morphogenetic protein CDMP-1 or a transforming growth factor β having at least 80% homology with CDMP-1, or a factor co-expressed and/or co-detectable therewith, is used as a marker of skeletal precursor cells from any part of a mammalian body.

8 Claims, 9 Drawing Sheets

A

B

ISOLATION OF SKELETAL PRECURSOR CELLS

This application is a divisional of, and claims priority from, U.S. patent application Ser. No. 10/089,994, filed Jul. 2, 2002, which is the U.S. National Stage of international application PCT/BE00/00120, filed Oct. 6, 2000, which, in turn, claims the benefit of European patent application 99203290.4, filed Oct. 7, 1999, and European patent application 99203274.8, filed Oct. 6, 1999.

The present invention relates to the field of tissue engineering in general, and more specifically to the identification of skeletal precursor cell populations for the repair of connective tissues, including skeletal tissue in vivo.

BACKGROUND OF THE INVENTION

Cartilage is a tissue composed by a cellular component, chondrocytes, and by an extracellular matrix typically rich in type II collagen and highly sulfated proteoglycans. The latter property confers cartilage its peculiar histochemical characteristics that are strong staining with alcian blue at low pH (0.2-2.5) and metachromasia with toluidine blue and safranin O. The abundance of type II collagen, link protein, and proteoglycan aggrecan, together with the presence of minor collagens such as type IX and type XI collagen, are hallmarks of cartilage tissue. In post-natal mammals cartilage contributes to the structure of several organs and systems like the articular surface of diarthrodial joints and other joint-associated structures such as menisci, the ear, the nose, the larynx, the trachea, the bronchi, structures of the heart valves, part of the costae, synchondroses, entheses etc. In some of the mentioned locations (e.g. entheses, the annulus fibrosus of the intervertebral disks, the menisci, insertion of ligaments etc.) for the abundance of collagens (mostly type I collagen) it is called fibrocartilage. In other locations (e.g. the pinna of the ear, epiglottis etc.) it is particularly rich of elastin and is called elastic cartilage. In all the other structures including articular cartilage, for its semi-transparent, clear aspect it is called hyaline cartilage.

During embryonic development of long bones, mesenchymal cells aggregate and differentiate to form cartilage anlagen, which provide the mold of the future long bones. These cartilage templates in development evolve undergoing endochondral bone formation through a cascade of events including chondrocyte hypertrophy, vascular invasion, mineralization, and eventually replacement by bone, except for a thin layer at the extremities of the bone elements that will differentiate into the articular surface of dyarthrodial joints. In this locations cartilage tissue remains hyaline for all the life-span of the individual. With aging, articular cartilage is well known to undergo a process of senescence, being affected in its mechanical properties and intrinsic resilience.

The current therapy for loss of cartilage tissue is replacement with a prosthetic material such as silicone for cosmetic repairs, or metal alloys for joint refinement. Placement of prosthetic devices, however, is a very artificial way of repairing, usually associated with loss of underlying bone without recovery of the full function allowed by the original cartilage tissue. Serious long-term complications associated with the presence of a permanent foreign body can include infection, erosion and instability. Implantation of sterilized bone or bone powder with surgical steel seeded with bone cells has been largely unsuccessful because of the non-degradable nature of the cell support. U.S. Pat. No. 4,609,551 discloses that fibroblasts exposed in vitro for at least three days to a soluble bone protein are capable of stimulating a chondrogenic response in vitro and/or in vivo. The activated fibroblasts are then transferred in vivo by combining them with a biodegradable matrix, or by intra-articular injection or attachment to allografts and prosthetic devices. The disadvantage of this method is that chondrogenesis is not allowed to develop in the short-term cultures and there is an unduly heavy reliance on the exposed fibroblasts at the implant site for cartilage synthesis. EP-A-739,631 discloses producing a biological material comprising reconstituted cartilage tissue by growing chondrocytes on a flexible sheet of 1.5 mm thick demineralized natural bone. This, however, will be useful only when the bone is not self-derived, because harvesting self-derived bone requires a complicated and painful surgery.

Joint surface defects can be the result of various etiologies such as inflammatory processes, neoplasias, post-traumatic and degenerative events, etc. Whatever the cause, due to its limited capacity for repair, cartilage heals poorly with, at best, some scar formation or fibrocartilaginous tissue. This partial repair of the articular surface leads to osteoarthritis and severe functional disability. Based on the depth of the injury, two types of joint surface defects are defined, the osteochondral (or full-thickness) and the superficial (or partial-thickness).

Osteochondral (or full-thickness) joint surface defects include damage to the articular cartilage, the underlying subchondral bone tissue, and the calcified layer of cartilage located between the articular cartilage and the subchondral bone. They typically arise during severe trauma of the joint or during the late stages of degenerative joint diseases, e.g. during osteoarthritis. Since the subchondral bone tissue is both innervated and vascularized, damage to this tissue may be painful. Osteochondral defects rely on the extrinsic mechanism for repair. Extrinsic healing relies on mesenchymal elements from subchondral bone or joint-associated tissues to participate in the formation of new connective tissue, including skeletal tissue. This repair tissue may undergo metaplastic changes to form fibrocartilage that does however not display the same biochemical composition or mechanical properties as normal articular cartilage or subchondral bone and degenerates with use.

Superficial or partial-thickness injuries of the articular cartilage that do not penetrate the subchondral bone rely on the intrinsic mechanism for repair. Soon after superficial injury, chondrocytes adjacent to the injured surfaces show a brief burst of mitotic activity associated with an increase in metabolic activity and matrix synthesis. Despite these attempts at repair, there is no appreciable increase in the bulk of cartilage matrix and the repair process is rarely effective in healing the defects. Although initially sometimes painless, partial-thickness defects often degenerate into osteoarthritis of the involved joint.

Repair of articular cartilage defects with suspensions of chondrocytes has been carried out in a variety of animal models and is now employed in humans (Brittberg M. et al., N. Eng. J. Med. 1994, 331:889-95). Autologous chondrocytes obtained from an unaffected area of the joint are released, expanded in vitro in the presence of autologous serum and subsequently injected under a periosteal flap sutured to cover the cartilage defect. This procedure has led to a proven at least symptomatic amelioration. This promising approach has still wide margins for improvement, since it is known that in vitro expansion of chondrocytes results, after a limited number of cell divisions, in a loss of their phenotypic stability (as defined by the ability of chondrocytes to form hyaline cartilage in vitro but also in vivo) making the cell suspension to be injected unreliable.

Three alternative approaches have been developed in an attempt to improve the success rate in treating mammalian articular cartilage defects. In the first approach, synthetic carrier matrices are impregnated with chondrocytes and then implanted into the cartilage defect where they hopefully produce and secrete components of the extracellular matrix to form articular cartilage at the site of the defect. A variety of synthetic carrier matrices have been used to date and include three-dimensional collagen gels (e.g. U.S. Pat. No. 4,846,835), reconstituted fibrin-thrombin gels (e.g. U.S. Pat. Nos. 4,642,120; 5,053,050 and 4,904,259), synthetic polymer matrices containing polyanhydride, polyorthoester, polyglycolic acid and copolymers thereof (U.S. Pat. No. 5,041,138), and hyaluronic acid-based polymers. Once a mitotically expanded population of chondrocytes is obtained, the cells can be implanted either back into the same subject from which their parental cells were originally derived (autologous implantation), or into a different subject (heterologous implantation). In addition, heterologous implantation may use chondrocytes obtained from a related or unrelated individual of the same species (allogeneic), or from a different species (xenogeneic). Alternatively, chondrocytes may be obtained from an established, long-term cell line that is either allogeneic or xenogeneic.

Autologous implantation requires that chondrocytes are harvested from an uninvolved area of the joint surface from the patient and then in vitro culture expanded to sufficient number or density for an effective implant. The amount of time required for such sufficient expansion, however, may preclude the effective use of an autologous culture since some cartilage repairs should be carried out immediately or within a short time after a traumatic injury occurs. Another limitation is the mitotic potential of the cells, since there is a limitation to the number of times the cells can be expanded, and the ultimate quantity of cells produced for therapy may be limited. In addition, where a severe debilitating joint disorder causes general degradation of cartilage tissue throughout a patient's body, namely e.g. in elderly people, there may be very little unaffected cartilage tissue available from which to initiate a chondrocyte culture. The introduction of heterologous chondrocytes into a patient, on the other hand, may stimulate an undesirable immune response directed against the implanted material, leading to potential rejection of the newly formed and engrafted cartilage tissue. In addition, heterologous implantation risks the transmission to the subject of infectious agent(s) present in the tissue or cell line.

Moreover, when using synthetic carrier matrices neo-cartilage may be formed around the periphery of the implant thereby preventing integration of the implant into the cartilage defect. Monitoring the formation and development of the resulting synthetic cartilage in situ is difficult to perform and usually involves an arthroscopic or open joint examination. Furthermore, implants containing synthetic polymer components may be unsuitable for repairing large cartilage defects since polymer hydrolysis in situ inhibits the formation of cartilage and/or its integration into the defect.

In the second approach, the defect is filled with a biocompatible, biodegradable matrix containing chemotactic and mitogenic growth factors to stimulate the influx of chondrocyte progenitor cells into the matrix in situ. The matrices optimally contain pores of sufficient dimensions to permit the influx into, and proliferation of the chondrocyte progenitors within the matrix. The matrix also may contain growth factors to stimulate the differentiation of chondrocyte progenitor cells into chondrocytes which in turn secrete extracellular matrix components to form cartilage at the site of the defect in situ (e.g. U.S. Pat. Nos. 5,206,023 and 5,270,300 and EP-A-530,804). This approach however results in problems similar to those associated with the first approach hereinabove. Furthermore there is no data so far that articular cartilage contains chondrocytic progenitors for partial-thickness defects.

In the third approach, chondrocytes may be cultured and expanded in vitro to form synthetic cartilage-like material that is implanted subsequently into the cartilage defect. This has the advantage over the previous methods in that the development of the synthetic cartilage material may be monitored, through biochemical and morphological characterization, prior to implantation. Growing chondrogenic cells may be achieved in either an anchorage-dependent or an anchorage-independent manner. In the latter, chondrogenic cells may be cultured as colonies within an agarose gel. Heretofore, only small pieces of cartilage tissue of undefined shape have been prepared using this manner. Furthermore, the resulting cartilage remains embedded within a gel matrix making it less suitable for implantation into mammals. Alternatively, in another anchorage-independent method, chondrocytes may be cultured as colonies in suspension culture. However the resulting particles containing synthetic cartilage-like material are usually small and of undefined shape thus making them unsuitable for implantation and repair of a predetermined articular cartilage defect. This would rather result in several little pieces of cartilage, completely separated from each other, and far from being very well integrated among them and the surrounding cartilaginous tissue.

In the anchorage-dependent method, primary cultures of chondrocytes isolated from primary tissue are grown as monolayers attached to the surface of a cell culture flask (e.g. U.S. Pat. No. 4,356,261). The primary cells derived directly from explant tissue remain capable of producing and secreting extracellular components characteristic of natural cartilage, specifically type II collagen and sulfated proteoglycans. However, it is well known that during in vitro expansion procedures chondrocytes in monolayer undergo a dedifferentiation process, thereby losing their ability to organize hyaline cartilage in vivo. Therefore, until now it has not been possible to prepare large patches of articular cartilage from small pieces of biopsy tissue using the anchorage-dependent procedures of U.S. Pat. No. 4,356,261.

In order to solve the above problems, U.S. Pat. No. 5,723,331 provides a method for preparing in vitro large quantities of synthetic cartilage from small samples of biopsy tissue which, based on the discovery that chondrogenic cells may be isolated from a variety of tissues, e.g. pre-existing cartilage, perichondrial tissue or bone marrow, and expanded in vitro prior to cartilage formation, includes first seeding denuded (i.e. isolated from an enzymatically or mechanically disaggregated tissue) chondrogenic cells, proliferated ex viva, into a pre-shaped well having a cell contacting, cell adhesive surface, and then culturing the proliferated chondrogenic cells in the well for a time sufficient to permit the cells to secrete an extracellular matrix thereby to form a three-dimensional, multi cell-layered patch of synthetic cartilage.

A further disadvantage of these methods is that the chondrocytes must be obtained from the patient, typically by a biopsy, culture expanded, and then implanted on a matrix. This is relatively easy in laboratory animals, but presents greater logistical problems in humans where a defect is created by the biopsy required to provide cells for repair of another defect. Mor over, if the defect includes a part of the underlying bone, this is not corrected using chondrocytes, which are already differentiated and will not form new bone. The bone is required to support the new cartilage.

The use of mesenchymal stem cells has also been proposed for the repair of many tissues including cartilage. Mesenchymal stem cells are a potential alternative source of cartilage producing cells. They are generally recognized as pluripotent cells which are capable of dividing many times to produce progeny cells that can eventually give rise to connective tissues, including cartilage, bone, tendons, ligaments, marrow stroma. By definition, they are not limited to a fixed number of mitotic divisions.

Stem cells are defined as cells that are undifferentiated, which can divide without limit to yield cells that are either stem cells or cells that further differentiate to yield different types of progenitor cells, including mesenchymal stem cells. Those mesenchymal stem cells are pluripotential cells that are capable of differentiating into any of the specific types of mesenchymal or connective tissues, including skeletal tissues. Mesenchymal stem cells were isolated from bone marrow or other sources such as periosteum, placenta, umbilical cord, skin, and blood (e.g. in U.S. Pat. No. 5,811,094). Pluripotent mesenchymal stem cells have also been isolated from muscle (Patè et al., *Proc. 49th Ann. Sess. Forum Fundamental Surg. Problems* October 1993, 587-9), heart (Dalton et al., *J. Cell Biol.* 1993, 119 R202) and granulation tissue (Lucas et al., *J. Cell. Biochem.* 1993, 122 R212). Pluripotency was demonstrated using a non-specific inducer, dexamethasone, which elicits differentiation of the stem cells into chondrocytes (cartilage), osteoblasts (bone), myotubes (muscle), adipocytes (fat), and connective tissue cells.

Unfortunately, although it is highly desirable to have stem cells which are easily obtained by a muscle or a skin biopsy, cultured to yield large numbers, and then used as a source of chondrocytes or osteoblasts or myocytes, there is no known specific inducer of the mesenchymal stem cells that yields only cartilage. In vitro studies in which differentiation is achieved yield a mixture of cell types. In U.S. Pat. Nos. 5,226,914 and 5,197,985 the cells were seeded into porous ceramic blocks and, subcutaneously implanted into nude mice, yielded primarily bone. However, U.S. Pat. No. 5,906,934 discloses that under very specific conditions mesenchymal stem cells in a suitable polymeric carrier (such as polyglycolic acid mesh) implanted into a cartilage and/or bone defect will differentiate to form cartilage and/or bone, as appropriate. Also U.S. Pat. No. 5,919,702 discloses chondrocyte progenitor cells isolated from umbilical cord sources, e.g. from Wharton's jelly, and cultured so as to give rise to chondrocytes that can produce cartilage tissue. Also in another attempt to avoid the drawbacks of current cartilage and bone repair techniques which cause bleeding and involve the use of mechanically weak non self-derived material, U.S. Pat. No. 5,866,415 suggests treating cartilage or bone defects with a biological material obtained by attaching in vitro cartilage or bone forming cells to a periosteum of sufficient size to accommodate the defect.

WO/96/41523 and WO96/41620 describe the use of FGFR3 as a marker for mesenchymal skeletal progenitor cells. Such cells, however, express FGFR3 which has been determined by the present inventors to indicate differentiation into non-pluripotent cells of the prechondroblast type in humans. Hence, the cells selected by these known methods differ from the precursor cells selected in accordance with the present invention.

FIG. 1 shows schematically the hierarchical cascade of cells in the differentiation process, starting from the undifferentiated mesenchymal stem cells downwards to the fully differentiated cells of the skeleton. U.S. Pat. No. 5,811,094 describes methods to identify, selectively isolate and enrich by culture expansion mesenchymal stem cells. Said patent does not provide methods for isolating, purifying, and culturally expanding skeletal precursor cells, methods which are the purpose of the present invention. Our efforts are focused on the skeletal precursor cells, as hereinafter defined, unraveling the molecular cascade of events underlying the differentiation pathways leading to the specialized cells of the skeletal tissues, with specific attention to the generation of the stable chondrocytes. Stable chondrocytes are assumed to form stable cartilage in vivo and/or in vitro under appropriate conditions. With stable cartilage is meant that any signs of bone formation remain absent, even over longer periods.

Transforming growth factor-.beta ("TGF-β") refers to a family of related dimeric proteins, which regulate the growth, and differentiation of many cell types. Members of this family include TGF-β 1, TGF-β 2, TGF-β 3, TGF-β 4, TGF-β 5, morphogenic proteins ("MP") such as MP-121 and MP-52, inhibins/activins (such as disclosed in EP-A-222,491), osteogenic proteins ("OP"), bone morphogenetic proteins (hereinafter denoted "BMP"), growth/differentiation factors ("GDF") such as GDF-5, GDF-6, GDF-9 and Nodal. TGF-β was first characterized for its effects on cell proliferation. It both stimulated the anchorage-independent growth of rat kidney fibroblasts and inhibited the growth of monkey kidney cells. TGF-β family members have been shown to have many diverse biological effects, e.g. they regulate bone formation, induce rat muscle cells to produce cartilage-specific macromolecules, inhibit the growth of early hematopoietic progenitor cells, T cells, B cells, mouse keratinocytes, and several human cancer cell lines. TGF-β family members increase the synthesis and secretion of collagen and fibronectin, accelerate healing of incisional wounds, suppress casein synthesis in mouse mammary explants, inhibits DNA synthesis in rat liver epithelial cells, stimulate the production of BFGF binding proteoglycans, modulate phosphorylation of the epidermal growth factor ("EGF") receptor and proliferation of epidermoid carcinoma cells and can lead to apoptosis in uterine epithelial cells, cultured hepatocytes and regressing liver. TGF-βs can mediate cardio-protection against reperfusion injury by inhibiting neutrophil adherence to endothelium and it protects against experimental autoimmune diseases in mice. On the whole, proteins of the TGF-β family are multifunctional, hormonally active growth factors and also have related biological activities such as chemotactic-attraction of cells, promotion of cell differentiation and tissue-inducing capabilities. Differences in their structure and their affinity for receptors lead to considerable variations in their exact biological function.

In contrast to the foregoing reports of the ability of TGF-β to induce the production of cartilage-specific macromolecules in muscle cells and chondrocytes, TGF-β was found to act synergistically with fibroblast growth factor to inhibit the synthesis of collagen type II by chicken sternal chondrocytes and in rat chondrocytes. In fact, TGF-β has emerged as the prototypical inhibitor of the proliferation of most normal cell types in vitro as well as in vivo, exhibiting a remarkable diversity of biological activity. TGF-β 1 has been purified from human and porcine blood platelets and recombinant TGF-β 1 is currently available.

Among the sub-family of BMPs, the structures of BMP-1 through BMP-13 have previously been elucidated. The unique inductive activities of these proteins, along with their presence in bone, suggests that they are important regulators of bone repair processes and may be involved in the normal maintenance of bone tissue. Recently, the BMP-12-related subfamily of proteins, including BMP-13 and MP52 (see e.g. WO93/16099 and U.S. Pat. No. 5,658,882), was shown to be useful in compositions for the induction of tendon/ligament-like tissue formation and repair. U.S. Pat. No. 5,902,785 discloses that BMP-12 related proteins are particularly effective for the induction of cartilaginous tissue and that BMP-9 is useful for increasing proteoglycan matrix synthesis and therefore for the maintenance of cartilaginous tissue. It also describes compositions comprising a BMP-12 related protein and additionally including one or more TGF-β proteins proven to be osteogenic, preferably BMP-2, -4, -5, -6 and/or BMP-7 as useful for the regeneration of multiple tissue types (for example at the interface or junction between tissues) and especially useful for the treatment of articular cartilage, in which the articular surface, cartilage, subchondral bone and/or tidemark interface between cartilage and bone need to be repaired. The same patent further describes compositions comprising a BMP-12 related protein together with a protein useful for the maintenance of chondrocytes or cartilaginous tissue such as BMP-9, the said compositions being especially useful for the induction and maintenance of cartilaginous tissue at a site in need of cartilage repair such as an articular cartilage defect.

WO96/14335 discloses, using mRNA prepared from newborn articular cartilage, the isolation of two members of the BMP family, designated Cartilage-derived morphogenetic proteins-1 and -2 (CDMP-1, CDMP-2). More specifically, WO96/14335 discloses a purified cartilage extract that stimulates local cartilage formation when combined with a matrix and implanted into a mammal, said extract being produced by obtaining cartilage tissue, homogenizing said cartilage tissue in the presence of chaotropic agents under conditions that permit separation of proteins from proteoglycans, separating said proteins from said proteoglycans, and obtaining said proteins. It also discloses an isolated DNA molecule encoding a protein having chondrogenic activity in vivo but substantially no osteogenic activity in vivo. The role of CDMP-1 as a regulator of skeletal growth is now well documented. Storm et al. (1994) in *Nature* 368, 639-43 and Chang et al. (1994) in *J. Biol. Chem.* 269, 28227-34 independently established that CDMP-1 mapped close to the brachypodism locus on chromosome 2 in mice and might be involved in the brachypodism phenotype. Also the expression patterns of CDMPs suggests an important role for these genes in joint morphogenesis. WO98/59035 also discloses a method of maintaining a cartilaginous phenotype in chondrocytes in vitro, comprising culturing the chondrocytes in a serum-free medium containing such a CDMP and/or BMP. Table 1 below summarizes the BMP superfamily members in mammals (Reddi A H, *Nature Biotechnol.* 1998, 16: 247-52).

TABLE 1

| BMP subfamily | Generic name | BMP designation |
|---|---|---|
| BMP 2/4 | BMP-2A | BMP-2 |
|  | BMP-2B | BMP-4 |
| BMP 3 | Osteogenin | BMP-3 |
|  | Growth/differentiation factor 10 | BMP-2B |
| Op-1/BMP-7 | BMP-5 | BMP-5 |
|  | Vegetal related-1 (Vgr-1) | BMP-6 |
|  | Osteogenic Protein-1 (Op-1) | BMP-7 |
|  | Osteogenic Protein-2 (Op-2) | BMP-8 |
|  | Osteogenic Protein-3 (Op-3) | BMP-8B |
|  | Growth/differentiation factor 2 (GDF-2) | BMP-9 |
|  | BMP-10 | BMP-10 |
|  | Growth/differentiation factor 11 (GDF-11) | BMP-11 |
| GDF-5,6,7 | Growth/differentiation factor 7 (GDF-7) or cartilage-derived morphogenetic protein-3 (CDMP-3) | BMP-12 |
|  | Growth/differentiation factor 6 (GDF-6) or cartilage-derived morphogenetic protein-2 (CDMP-2) | BMP-13 |
|  | Growth/differentiation factor 5 (GDF-5) or cartilage-derived morphogenetic protein-1 (CDMP-1) | BMP-14 |
|  | BMP-15 | BMP-15 |

Other families of growth factors have been shown to be involved in cartilage differentiation and maintenance such as the fibroblast growth factors (FGFs), which are a family of polypeptide growth factors involved in a variety of activities. One of their receptors, FGF receptor 3 (FGFR-3) (Keegan K. et al., 1991 Proc. Nat. Acad. Sci. 88: 1095-99), is known to play a crucial role in chondrogenesis. Point mutations in the fgfr3 gene resulting in a ligand-independent constitutively active protein (which means that the FGF signaling is always active also in the absence of the ligand) cause skeletal abnormalities as achondroplasia and thanatophoric dysplasia.

As already outlined in page 2, although autologous chondrocyte transplantation ("ACT") is becoming a widely accepted technique for repair of joint surface defects ("JSD"), it still presents some drawbacks. More in detail, this procedure implies in vitro expansion—in the presence of autologous serum—of autologous chondrocytes obtained from an uninvolved area of the joint, followed by the implantation of the chondrocyte suspension under a periosteal flap sutured to seal the joint surface defect. Cell expansion is necessary to obtain from a small cartilage biopsy a number of cells sufficient to repair the cartilage defect. However, it is well known, as explained before, that in vitro expansion of chondrocytes results in cell de-differentiation. This implies that chondrocyte expansion pays the price of loss of phenotypic stability. Therefore, a quality control for expanded chondrocytes to be used for ACT is needed. At the end of cell expansion the chondrocyte population is composed of some cells that retain their phenotypic stability, and others that still can proliferate but will not anymore contribute to cartilage repair. In order to obtain a consistent cell suspension for ACT, it is desirable to select stable chondrocytes within the expanded cell population. Chondrocytes are skeletal cells able to grow in anchorage-independent agarose cultures. The ability of chondrocytes to grow in anchorage-independent conditions is critical for those cells to survive and organize cartilage tissue once injected as a cell suspension for repair of JSD, but is probably not the only phenotypic trait required.

Therefore there is a need in the art for identifying and selecting an easily accessible and expandable source of pluripotent skeletal precursor cells. There is a need in the art for solving the various problems encountered in the cartilage repair known methods. There is also a need in the art for developing repair techniques for connective tissues including cartilage, e.g. for medical problems such as rheumatoid arthritis and osteoarthritis, and a long felt need for quality control on the chondrocyte populations used for such purposes. There are a number of suggestions in the prior art that some mesenchymal stem cells could specifically yield cartilage or, as needed, other connective tissues. For instance bone marrow contains populations of pluripotent mesenchymal stem cells having the capacity to differentiate into a wide range of cell types of the mesenchymal, hematopoietic and stromal lineages. It is also known that mesenchymal stem cells cultured in vitro can be induced to differentiate into bone or cartilage in vivo and in vitro, depending upon the tissue environment or the culture medium into which the cells are placed. To date, however, very few common cell markers or differentiation antigens were identified. Examples of such markers include Ly-6 antigens for murine osteoblasts (see Horowitz et al. (1994) in *Endocrinology*, 135, 1032-43) and CD34 for human hematopoietic cell types. On the other hand, periosteum and marrow are known as the most common sources of precursor cells having osteogenic potential. More specifically it has been shown that cells from marrow, when isolated and expanded by the culture method of Friedenstein, will form bone, cartilage and fibrous tissue when implanted. However Friedenstein in *Calcif. Tiss. Int.* (1995) 56(S):S 17 admitted that obstacles, such as the need for culturing for several passages and developing a method for transplanting such cells, must be overcome before clinical utility of this discovery can be confirmed. Therefore there is a need in the art for the proper identification of pluripotent skeletal precursor cells in a wide range of easily accessible and expandable sources. These goals and other purposes are achieved by means of the following objects of the present invention.

SUMMARY OF THE INVENTION

A first object of the pr sent invention is the identification and characterization of skeletal precursor cells in a wide range of easily accessible and expandable sources. Easily accessible tissues include among others, periosteum, bone marrow and synovial membrane. The solution to this problem in accordance with the present invention is to use a set of molecular markers. These molecular markers may be either positive markers, indicating precursor cells which are pluripotent or negative markers indicating that the cells have differentiated and are no longer pluripotent. Absence of a negative marker can be used as a positive marker. A second object of the present invention is the use of such skeletal precursor cells and molecular markers for the repair of a wide range of connective tissues. A third object of the present invention is the use of such skeletal precursor cells as a source of transforming growth factors ("TGF") linked to the phenotypic stability of a certain cell population involved in a certain differentiation pathway, such as for instance members of the TGF-$\beta$ family which are positively associated with chondrocyte phenotypic stability. A fourth object of the present invention is the use of such skeletal precursor cells and molecular markers as matrix producing cells in tissue engineering procedures. A fifth object of the present invention is the co-implantation of expanded skeletal precursor cells and chondrocytes for in vivo cartilage repair.

DETAILED DESCRIPTION OF THE INVENTION

Figure 1:
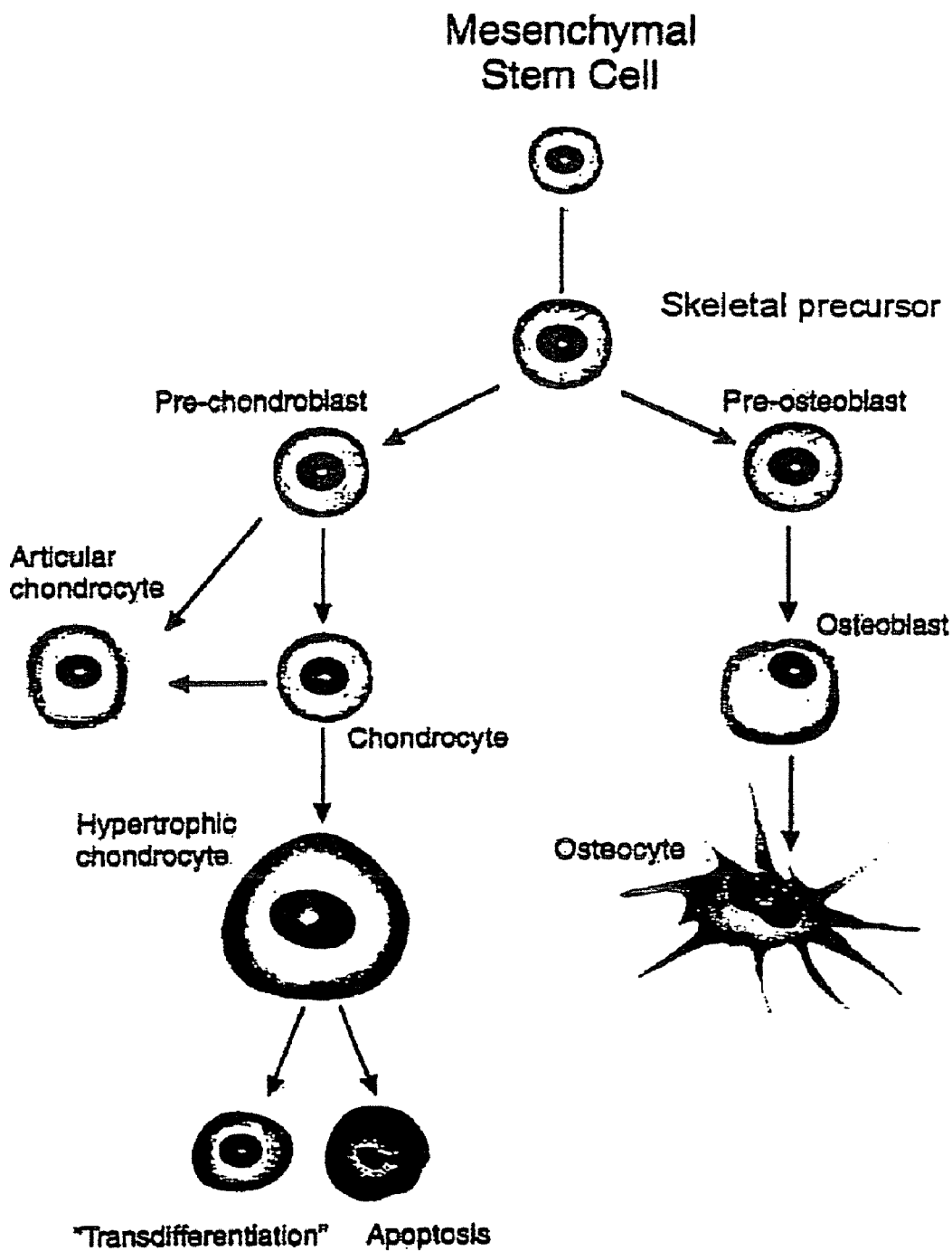
FIG. 1 is a schematic representation of the hierarchical cascade of cells in the differentiation pathways.

Terms used throughout this disclosure are defined as follows:

Chondrocyte Stability

The capacity of a cell suspension (either obtained from cartilage tissue or from any other tissue containing cells with chondrogenic potential) to produce in vitro and/or upon injection in a mammal (in vivo), such as immune-deficient mice, in a time frame of 2-3 weeks a true-to-type (hyaline) cartilage implant without signs of vascular invasion or endochondral bone formation Chondrogenic The capacity to promote or stimulate cartilage growth, as applied to chondrocytes and to cells which themselves differentiate into chondrocytes. The term also applies to certain growth factors, such as TGF-$\beta$, which promote cartilage growth.

Co-expression

With co-expression, in the context of the present invention, is meant that a factor is expressed whenever another factor or marker is expressed in or on a cell. For instance, where a morphogenic protein is used as a marker, and more in particular the cartilage-derived morphogenic protein CDMP-1 or a homolog thereof are/is expressed, co-expression requires that a co-expressed marker is only present or expressed when the morphogenic marker is expressed. Hence, the factor is linked with the same specific post-natal differentiation pathway as the morphogenic protein it co-expresses with, such as CDMP-1. It preferentially is upregulated/downregulated together with the marker. It will for instance downregulate when the precursor cells undergo differentiation such as towards the chondrocytic phenotype. Such co-expressing marker further is preferably expressed at detectable levels. Such co-expressed factor can be a recognizable cell surface marker, detectable via polyclonal or monoclonal antibodies and/or specific ligands. The co-expressed factor may also include any functional or structural homolog of CDMP-1.

Connective Tissue

As used herein, any of a number of structural tissues in the body of a mammal including bone, cartilage, ligament, tendon, meniscus, muscle, dermis, hyperdermis and joint capsule.

Differentiation

A biological process by which primitive unspecialized cells through a series of cellular divisions give rise to progeny having more an more specialized function(s). Terminal differentiation provides a highly specialized cell having unique functional, genetic and phenotypic characteristics.

Heterologous

Refers to any gene, promoter, polypeptide or other molecule that is not naturally present in, not native to a wild-type version of a referenced cell. For example, an *E. coli* β-galactosidase gene is considered to be "heterologous" to a human skeletal precursor cell.

Mesenchymal Stem Cell

A primitive cell type having the capacity for self-regeneration and for differentiation through a series of lineages to produce progeny cells with wide phenotypic variety including connective tissues, marrow stroma, adipocytes, dermis and muscle.

Marker Protein

A polypeptide that distinguishes one cell (or set of cells) from another cell (or set of cells) in a population of cells. For example, a polypeptide that is expressed (either naturally or artificially, e.g., introduced by genetic engineering) on the surface of skeletal precursor cells but not other cells of a cell population serves as a marker protein for the skeletal precursor cells. Typically, the marker protein is a cell-surface antigen, like for instance a growth hormone receptor, such that antibodies that bind the marker protein can be used in cell sorting methods, e.g., to produce a population of cells enriched for cells that express the marker protein. Alternatively, intracellular proteins can be used as marker proteins. For example, fluorescent or luminescent proteins, such as green fluorescent protein e.g. aequorin (green fluorescent protein of *Aequoria victoria*) (Tanahashi et al (1990), Gene 96: 249-255) can be used as the marker protein and can facilitate cell sorting, e.g., by FACS. Also enzymes can be used, provided that the activity of the enzyme can be detected. For example, β-galactosidase is well suited for use as a marker protein; this enzyme can be detected by introducing into the cell a substrate(s) that release a fluorescent product(s) upon cleavage by the enzyme (available from, e.g., Molecular Probes). Another suitable enzyme is catechol 2,3-dioxygenase, which is encoded by xy/E of *Pseudomonas putida* (Domen et al (1986), Anal. Biochem. 155: 379-384).

Operably Linked

Connection of a coding sequence and (a) regulatory sequence(s) (e.g., a promoter) in such a way as to permit gene expression when the appropriate molecules (e.g., transcriptional activator proteins) are bound to the regulatory sequence(s).

Osteogenic

The capacity to promote or generate the production of bone. The term may be applied to osteoblasts which have the capacity to promote bone growth, or to cells which themselves are able to differentiate into osteoblasts. The term would also apply to growth factors having the ability to promote bone growth.

Phenotypic Stability

Maintenance of the ability of any cell to organize or reorganize, in vivo or in vitro, the structure of a specific tissue, either the original tissue where the cells were taken from, or a different tissue the cells have been forced to form under specific conditions.

Precursor Cell

A cell having the capacity of undergoing differentiation to perform a specific function.

Promoter

A nucleotide sequence sufficient to direct and/or regulate transcription of a coding sequence. Included within the invention are those promoters that are inducible by external signals or agents; such elements can be located in the 5' or 3' untranslated regions (UTR) and in the introns of the native gene. A "CDMP-1 promoter" is any sequence located in cis that is sufficient to direct and/or regulate expression of CDMP-1 in skeletal precursor cells. It is recognized that in genetic constructs containing a CDMP-1 promoter (e.g., those constructs that also contain a reporter gene or a gene encoding a marker protein), minor variations (e.g., deletions, point mutations, and the like) can be made in the sequence of the CDMP-1 promoter without abrogating its ability to be active in skeletal precursor cells and inactive in any other cells. Thus, CDMP-1 promoters having such minor variations without abrogating the skeletal precursor cell specificity of the promoter are encompassed by the term "CDMP-1 promoter". In addition, multiple copies of the CDMP-1 promoter, arranged in tandem, can be used to direct gene expression.

Relevant

Relevant, within the present context, refers to the fact that the gene product used to identify skeletal precursor cells, must be a product linked to the post-natal skeletal pathway in a way as CDMP-1 does.

Reporter Gene

Any gene for which expression can be monitored. Commonly used reporter genes include, for example, genes encoding chloramphenicol acetyltransferase, alkaline phosphatase, luciferase, and green fluorescent protein.

Skeletal Precursor Cell

A cell no longer undifferentiated, but already committed towards any of the differentiation pathways of the skeletal tissues. The cell is still pluripotent and may differentiate into any of the connective tissues or a sub-group thereof.

Skeletal Tissues

Skeletal tissues include teeth, bone, cartilage, meniscus, ligaments, intervertrebal discs, and muscle tissues.

Stable Cartilage

Cartilage not finally turning into bone, i.e. cartilage devoid of any signs of vascularization. Contrary to stable cartilage, transient cartilage in the end will become bone tissue. In the context of the present invention, cartilage is said to be stable if, even after e.g. seven weeks, any signs of bone formation are absent.

Stem Cell

Pluripotent precursor cell having the ability to self-renew and to generate a variety of differentiated cell types. True stem cells can divide indefinitely. With embryonic stem cells are understood the pluripotent cells of normal karyotype derived from a mammal's inner cell mass or blastocyst.

DETAILED DESCRIPTION

The present invention will mainly be described with reference to skeletal precursor cells but the invention is not limited thereto. The present invention relates to the use of embryonic markers which identify that certain precursor cells have entered a post-natal differentiation pathway. Its is believed that the present invention is not limited in any way as to cell type provided they are associated with organisms with differentiated cells. Examples are animals, especially mammals, insects or plants. The present invention is particularly useful with respect to mammalian precursor cells, in particular, skeletal precursor cells, more in particular skeletal precursor cells of humans and horses, but is not limited thereto. The present invention makes use of cell embryonic markers which are considered to be available in or on all differentiated cells or precursor cells of such differentiated cells in any differentiated life form. Such embryonic markers are considered to be a necessary part of or to be associated with a necessary part of embryogenesis as the growing organism during differentiation has also the necessity of identifying differentiated or partly differentiated cells and this must be achieved biochemically. Hence, the present invention has wide application.

The present invention is based upon surprising discoveries that have general relevance to the development of all differentiated life-forms, in particular mammals such as humans or horses.

First, pluripotent human skeletal precursor cells can be reliably identified by a set of molecular markers. The markers may be both positive, indicating the presence of the pluripotent precursor cells or negative, indicating that the cells have differentiated and are no longer precursor cells. The absence of negative markers can be a positive marker. Particularly, the present invention includes cells having the absence of a negative marker such as FGFR3 combined with the presence of a positive marker. Secondly, such skeletal precursor cells upon consistent and proper conditions are able to produce and repair various connective tissues including cartilage, when used either alone or in association with chondrocytes. And thirdly, such skeletal precursor cells can be induced to express genes linked to specific tissues.

Evidence is provided that the expression of CDMP-1 qualifies a certain culture expanded cell population as skeletal precursor cells. This is an unexpected result, since CDMP-1 has always been known to promote chondrogenic differentiation and never linked to the phenotype of skeletal precursor cells. Regardless of the source, cells are culture expanded and assessed by RT-PCR analysis for the expression of CDMP-1. Only the CDMP-1 expressing cells can be successfully processed to be directed into a specific differentiation pathway of any skeletal connective tissue, including cartilage. Interestingly, whenever a skeletal precursor cell as defined by the expression in RT-PCR of CDMP-1, undergoes differentiation such as towards the chondrocytic phenotype, entering a specific differentiation pathway is always preceded by the downregulation of the expression of CDMP-1.

A first embodiment of the present invention consists of the use of cartilage-derived morphogenetic protein CDMP-1 or a transforming growth factor having at least 80% homology with CDMP-1 as a positive marker of skeletal precursor cells from any part of a mammalian body or use of a factor or marker which is co-expressed or is co-detectable with CDMP-1. In other words, regardless of the source of cells, CDMP-1 or a homolog thereof or a co-expressed marker or factor is selectively expressed by skeletal precursor cells, and is downregulated as soon as said skeletal precursor cells undergo a differentiation step towards any mature lineage. For instance, when skeletal precursor cells differentiate into chondrocytes, the expression of cartilage markers such as type II collagen, FGFR3, type IX collagen, or type XI collagen, is always preceded by the disappearance of CDMP-1. Markers such as FGFR3, type II collagen, type IX collagen, or type XI collagen or markers or factors co-expressed or co-detectable with these markers are negative markers. Relevant gene products co-expressed with CDMP-1 or a CDMP-1 related gene can be us d in accordance with the present invention to identify positively skeletal precursor cells within a reference population. The absence of a negative marker may be used as a positive marker in accordance with the present invention. This first embodiment is based upon the characterization of human skeletal precursor cells from donors of various ages (ranging from 9 to 95 years old) over a large number of passages by molecular markers. Using reverse transcriptase polymerase chain reaction ("RT-PCR") analysis, it was observed that skeletal precursor cells are phenotypically stable throughout serial passaging, retaining their phenotype and their potential of differentiation even after having been frozen in liquid nitrogen for 18 months. Identification of CDMP-1 positive cells can be done at the DNA, RNA or protein level, directly via the gene and gene products of CDMP-1 or indirectly via functional homologs thereof or via factors or markers co-expressed with CDMP-1.

A second embodiment of the present invention consists of further using reagents, ligands and/or antibodies recognizing specific factors co-expressed with the morphogenic proteins in question, like cell surface markers. Such markers can be used for sorting of a heterogeneous mammalian cell pool, skeletal precursor cell sub-populations for further processing by proper treatment, like further differentiation along the specific lineage, e.g. differentiation into chondrocytes and preferentially stable chondrocytes. Cell sorting is based on the use of autologous or heterologous marker proteins. The heterologous marker protein can be viral, prokaryotic, eukaryotic or synthetic in origin. The marker protein can be a marker that when expressed results in preferential survival of cells expressing the marker, with antibiotic resistance being one such example. The selectable marker may also be a marker whose expression results in preferential killing of cells expressing the marker. In this case the marker is expressed in cells other than skeletal precursor cells. More typically, however, the marker protein is a polypeptide that is expressed on the cell surface. Examples of suitable marker proteins include CD8, β-galactosidase, catechol 2,3-dioxygenase, aequorin (green fluorescent protein of *Aequorea victoria*), and influenza virus hemagglutinin. The genes encoding these and other suitable marker proteins are known in the art. Conventional cell sorting methods (e.g., fluorescence-activated cell sorting (FACS)) can be used to isolate those cells in which the cell surface marker, co-detectable with CDMP-1 or a homolog thereof, is expressed. A fluorescently-labelled antibody is then used to specifically bind a cell surface polypeptide used as the heterologous marker. Alternatively, an unlabeled antibody can be use to specifically bind the cell surface polypeptide, and a second, labeled antibody can then be us d to specifically bind the first antibody. The fluorescently-tagged precursor cells can then be sorted away from other cells in the sample by FACS, for example. Other techniques, such as the use of protein-conjugated magnetic beads that selectively bind particular cells, can also be used. Suitable kits are commercially available. Generally, such kits utilize a tagged antibody (e.g., a biotin-tagged antibody) to bind the cell surface marker protein. The antibody-bound cells are contacted with a magnetic bead-protein conjugate, where the protein portion of the bead-protein conjugate specifically binds the tagged antibody. For example, a streptavidin-magnetic bead conjugate can be used to bind a biotin-tagged antibody to produce a complex containing the magnetic bead-protein conjugate, the tagged antibody, and the cell expressing the marker protein. Such complexes can be separated from other cells by temporarily adhering the complex to a magnet and separating the adhered cells from the other cells (i.e., a population of cells depleted for, e.g., skeletal precursor cells). Magnetic beads that are covalently coupled to a secondary antibody are commercially available. Other antibody-based methods for sorting cells, like the use of affinity chromatography or the retaining of cells expressing the particular cell surface proteins via Petri dishes coated with antibodies directed against the latter, also are known in the art and can be used in the invention. A useful, commercially available affinity cell separation kit, "CEPRATE LC", may be obtained from CellPro (CellPro, Inc. Bothell, Wash. 98021). Methods for raising IgM or IgG antibodies are well known in the art and are for instance described In Ausubel et al (ed), Short Protocols in *Molecular Biology*, 4$^{th}$ edition, John Wiley & Sons, New York, and more specifically units 11.3, 11.4 and 11.5; In Paul (ed), Fundamental immunology, 4$^{th}$ edition, Lippincott-Raven Publishers, New York, and more specifically chapter 4, p 101 ef; de St. Groth and Scheidegger (1980), *J Immunol Methods* 35:1-21; French et al (1986), *Immunol Today* 7:344-346; Langone and Vunakis (1986), *Methods in Enzymology*, vol 121, *Immunochemical Techniques. Part I, Hybridoma technology and monoclonal antibodies*. Orlando: Academic Press; Hämmerling et al (1981), *Monoclonal antibodies and T-cell hybridomas. Perspectives and technical advances*. Amsterdam: Elsevier/North-Holland Biomedical Press; Yokoyama (1995) In Coligan et al (ed), *Current protocols in immunology*, Wiley & Sons, New York, 2.5.1-2.2.17; Kohler and Milstein (1975), *Nature* 256: 495-497. It is also possible to select for skeletal precursor cells via reporter genes under control of a promoter expressed only in the precursor cells or at the contrary, in all cells but the envisaged precursor cells. Such reporter constructs may be used e.g. for study, e.g. to verify whether cells with a particle promoter being active possess the desired properties. A genetic construct (reporter construct) may therefore be introduced into the reference population of cells. The genetic construct includes then for instance a CDMP-1 promoter that is operably linked to a gene encoding a marker protein. The marker protein is a protein that is heterologous to the wild-type cells of the reference population, and that preferably is not expressed in the wild-type reference population and the skeletal precursor cells more in particular. Cells that express the marker protein (i.e. cells in which the CMDP-1 promoter is active) are then isolated in order to produce a population of cells enriched for chondrogenic skeletal precursor cells. Of course, by removing the CDMP-1-expressing cells from the cell population, this method can be used to produce a population of cells depleted of chondrogenic skeletal precursor cells. Methods for making the reporter construct and for introducing it into the reference population are known in the art. For instance, cells obtained from periosteum, synovial membrane or bone marrow can be transduced with a plasmid in which the expression of conventional dominant selectable markers such as those conferring resistance to antibiotics, e.g., neomycin phosphotransferase, of luminescent or fluorescent or proteins such as luciferase or green fluorescent protein (e.g. aequorin), of other detectable enzymes such as β-glucuronidase, or of cell surface proteins such as CD8 is brought under the control of the human CDMP-1 promoter. A putative promoter of CDMP-1 is disclosed in Sugiura T. et al, Biochem Biophys Res Comm 1999, 263:707-13. In addition, BAC clones isolated from the mouse CDMP-1 (GDF-5) locus, were modified by homologous recombination in bacteria. The resulting constructs drove the expression of exogenous reporter genes in developing mice of transgenic mice, Rountree R. et al, International Conference on Bone Morphogenetic Proteins, Jun. 7-11, 2000. The amount of G418 that would kill non-transformed cells varies upon the specific properties of the cells used. In general, the concentration is between 100 and 1000 μg/ml of active G418.

Suitable selection methods are well known in the art. Such selection or enrichment protocols will avoid the unpleasant eventuality of other contaminating tissues arising from the pool of skeletal precursor cells. Once enriched, these cells can be directed to any differentiation pathway such as the chondrogenic pathway, by culturing under consistent and appropriate conditions with or without morphogens/growth factors to end up with a homogeneous cell population, such as chondrocytes with a phenotypic stability. In particular, the present invention shows that periosteum, bone marrow, and synovial membrane contain CDMP-1 expressing skeletal precursor cells that can be committed towards chondrogenesis using appropriate culture conditions. In contrast to previous studies of Nakahara et al. (1991), *J. Orthop. Res.* 9:465-76, the present invention shows that regardless of donor age, human skeletal precursor cells are easily accessible and expandable and can be induced consistently to differentiate into chondrocytes.

A third embodiment of the present invention is the use of the positively marked, e.g. CDMP-1 marked, skeletal precursor cells for producing or repairing connective tissue in general, including trachea, cardiac valves, vocal cords and the like. This further use is based on the capacity of such skeletal precursor cells to retain the intrinsic potential of multilineage differentiation, which make them good candidates for tissue engineering protocols. Isolation, expansion and sorting cell populations using the specific markers of the invention lead to the proper cell pool suitable for such repair procedures. More specifically, using positively, marked, e.g. CDMP-1 marked, skeletal precursor cells, proper culture conditions have been developed leading to the induction and formation of cartilage in vitro. In the present invention, the formation of "stable cartilage" is among others envisaged. Stable cartilage in vivo is for instance obtainable from young periosteum-derived cells (PDCs). With young PDCs is meant that the cells are derived from individuals younger than 20 years, in particular younger than 16 and most in particular younger than 10. It is important to note that treatment of skeletal precursor cells in monolayer culture with various growth factors did not result in any response in terms of osteogenesis and/or chondrogenesis, as assessed by RT-PCR analysis for bone and cartilage markers, by alcian blue and von Kossa staining, and by alkaline phosphatase activity. For successful induction of cartilage, it appears necessary to culture CDMP-1 marked skeletal precursor cells at a very high cell density, for instance a cell density of at least $10^5$ cells/ml, and preferably in the so-called micromass culture at a cell density of about $2 \times 10^7$ cells/ml. For successful induction of connective tissue, it is further advisable to add (in vitro) or administer (in vivo) a factor that stimulates differentiation of the skeletal precursor cells into the type of connective tissue to be produced or repaired, e.g. a transforming growth factor-β such as TGF-β 1, TGF-β 2, or TGF-β 3, preferably at a rate of about 10 ng/ml in a chemically defined serum-free medium, to or together with the culture expanded CDMP-1 marked skeletal precursor cells. For instance, human PDCs from young donors exhibit spontaneous chondrogenic activity, but induction of a chondrogenic response in older cells was possible by combining micromass culture with e.g. TGF-β 1 treatment, independently from the number of cell passages or the age of the screened donors.

A fourth embodiment of the present invention is the use of the positively, e.g. CDMP-1 marked, skeletal precursor cells as a source of growth factors, more specifically Transforming Growth Factors-β ("TGF-β") and Bone Morphogenetic Proteins ("BMP") known to be important in the stimulation and maintenance of the cartilage phenotype. This can help for instance for chondrocyte in vitro expansion, preventing chondrocytes from de-differentiation through serial passaging. This may be useful for the in vitro expansion procedure of human chondrocytes for transplantation using a medium derived from autologous skeletal precursor cells.

A fifth embodiment of the present invention is the use of positively marked, e.g. CDMP-1 marked, skeletal precursor cells as matrix producing cells. According to this embodiment, human skeletal precursor cells treated with appropriate growth factors (as in the third embodiment hereinabove) are able to produce extracellular matrix reminiscent of hyaline cartilage. The said treated cells can therefore be used as a matrix supply for the attachment and growth of chondrocytes in joint surface defects ("JSD") repair, and for tissue engineering procedures of the cartilaginous skeleton in general, e.g. for the treatment of subglottic stenosis, tracheomalacia, chondromalacia patellae, osteoarthritis and traumatic lesions, for instance using bioresorbable polymers (such as polylactic acid or polyglycolic acid) locally applied to fill the lesion. In such a use, the said treated cells provide proper support for attachment and cell growth, eventually coated or mixed with growth factors. Such combinations of cells, polymer matrices and growth factors will also be useful in orthopedic reconstructive surgery. An alternative for this embodiment is a method for enhancing the implantation of a prosthetic device in connective tissue comprising the step of implanting a prosthetic device having skeletal precursor cells adhered thereto under conditions suitable for differentiating the cells into the connective tissue desired.

A sixth embodiment of the present invention is the co-implantation of positively marked, e.g. CDMP-1 marked, skeletal precursor cells and chondrocytes for JSD repair and tissue engineering procedures of the cartilaginous skeleton in general. This embodiment is based on the surprising observation that the addition of expanded skeletal precursor cells to a chondrocyte suspension for cartilage repair has a dramatic impact on the ability of cartilage formation by chondrocytes, both in vitro and in vivo. The said co-implantation is able to substantially reduce the number of chondrocytes needed for successful JSD repair and it also results in a remarkable enhancement of the amount of cartilage produced. These observations may allow us using freshly isolated chondrocytes or minimally expanded chondrocytes instead of the impaired in vitro expanded chondrocytic cells, thus circumventing the problem related to the loss of cartilage-forming ability of chondrocytes resulting from in vitro expansion. As is well known in the art, in vitro cell expansion is in fact a critical step in autologous chondrocyte transplantation and can hamper the effectiveness of the injected cells in producing cartilage.

In addition to the numerous previously cited uses, the positively marked, e.g. CDMP-1 marked, skeletal precursor cells of the present invention have the advantage that they can be stored up to at least 18 months in cell banks under storage conditions including a storage temperature below $-100°$ C., e.g. in liquid nitrogen, and in case of necessity thawed, properly treated, and implanted in the same individual at a site where new connective tissue is desired. For example, trypisin released PDC cultures were cryopreserved in liquid nitrogen in DMEM with 20% FBS and 10% dimethylsulfoxide (DMSO; Sigma). This storage capability of precursor cells is surprising, since other cells including chondrocytes lose their phenotype when stored under the same conditions even for a short time.

The positively marked, e.g. CDMP-1 marked, skeletal precursor cells can also be used for heterologous transplantation in cases of HLA (Human Leukocyte Antigen) compatibility or for tissues where the risk of rejection is minimal and can be easily prevented pharmaceutically.

Positively marked cells in accordance with the present invention may also exhibit absence of a negative marker. The cell sorting methods described above may be used to produce substantially pure precursor cells.

A more complete understanding of the present invention will be obtained by referring to the following illustrative examples.

EXAMPLE 1

Isolation of Skeletal Precursor Cells from Periosteum, Synovial Membrane, and Bone Marrow Periosteum from human donors of various ages was aseptically harvested from the proximal medial tibia, either within 12 to 24 hours after death or from patients undergoing surgical knee replacement. Periosteum was rinsed twice with Hank's Balanced Salt Solution ("HBSS") available from Life Technologies, supplemented with antibiotic-antimycotic solution (100 units/ml penicillin, 100 µg/ml of streptomycin, and 0.25 µg/ml of amphotericin B, also available from Life Technologies), finely minced, and digested with 0.2% collagenase (Life Technologies) in high-glucose Dulbecco's Modified Eagle Medium ("DMEM") (Life Technologies) containing 10% fetal bovine serum (FBS) (available from BioWhittaker) and antibiotics. After overnight incubation at $37°$ C., periosteal cells were collected by centrifugation, washed twice, resuspended in high-glucose DMEM supplemented with 10% FBS and antibiotics, plated in a T25 culture flask, and allowed to attach for 4 days. After that period of time, non-adherent cells were removed by changing the medium.

Synovial membrane from human donors of various ages was aseptically harvested from the knee joints within 24 hours after death, and processed following the same protocol described above for periosteum.

Heparinized bone marrow samples from human donors of various ages were diluted with HBSS, layered onto Lymphoprep (1.077 g/ml, available from Nycomed, Oslo), and centrifuged at 300×g for 20 minutes. Cells from the gradient interface were collected, washed three times in HBSS, and resuspended in medium for culture.

EXAMPLE 2

In Vitro Cell Expansion

Cells isolated according to example 1 were cultured in monolayer in high-glucose DMEM containing 10% FBS and antibiotics at $37°$ C. in 95% humidified air and 5% $CO_2$, and the medium was replaced every 3 days. After 10 to 20 days of primary culture, when the sparsely attached cells reached confluence, they were washed twice with calcium and magnesium-free phosphate buffered saline (PBS) and harvested by treatment with trypsin-EDTA (0.25% trypsin, 1 mM EDTA; Life Technologies), and replated by a 1:4 dilution for the first subculture. Cell passages were continued in the same way with a 1:4 dilution every 6-12 days and more preferably every 7-8 days when cells reached confluence.

EXAMPLE 3

CDMP-1 as a Marker of Skeletal Precursor Cells

Cells isolated as described in example 1 from periosteum, synovial membrane, and bone marrow, and expanded as described in example 2, were characterized at different passages by RT-PCR analysis as hereinafter described along with other cells such as human skin fibroblasts. CDMP-1 was found expressed only by skeletal precursor cell populations at all the passages examined up to 18, and not by other cell populations. We indeed demonstrated that only the CDMP-1 marked culture expanded cells under specific conditions can differentiate e.g. towards chondrogenesis, while the CDMP-1 negative cells under the same conditions are not capable of undertaking any skeletal differentiation pathway. Furthermore, the appearance of cartilage markers is always preceded by the downregulation of the expression of CDMP-1.

Figure 2A:
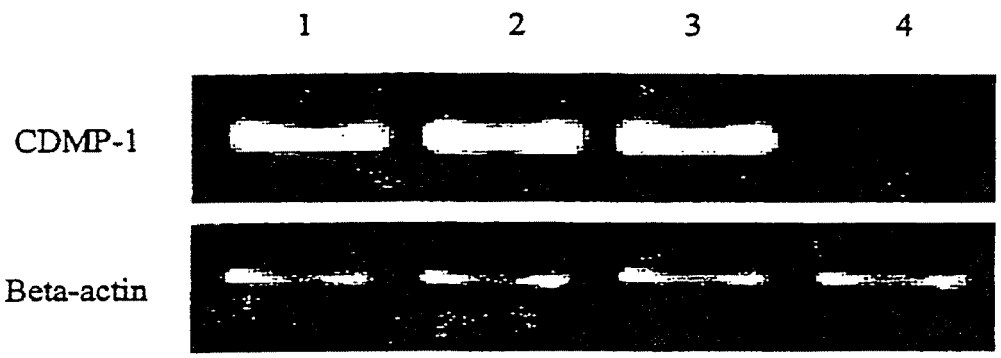
FIG. 2 is a picture showing that skeletal precursor cells express CDMP-1.

FIG. 2A shows RT-PCR analysis for the expression of CDMP-1 normalized to the expression of β-actin in different cell populations numbered from 1 to 4.

Lane 1: human periosteum-derived skeletal precursor cells;
Lane 2: human synovial membrane-derived skeletal precursor cells;
Lane 3: human bone marrow-derived skeletal precursor cells;
Lane 4: human skin fibroblasts.

Figure 2B:
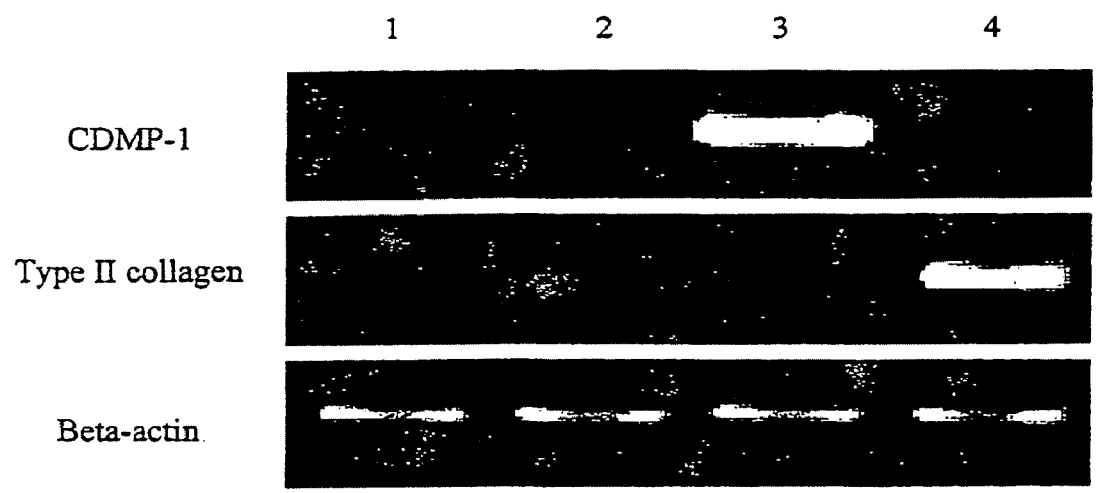

FIG. 2B shows RT-PCR analysis for CDMP-1 and type II collagen, normalized to the expression of β-actin, in human skin fibroblasts (lanes 1 and 2) and human periosteum-derived skeletal precursor cells (lanes 3 and 4) in micromass culture, either untreated (lanes 1 and 3) or treated for 6 days with 10 ng/ml TGF-β1 (lanes 2 and 4).

Lane 1: human skin fibroblasts untreated;
Lane 2: human skin fibroblasts treated with 10 ng/ml TGF-β1;
Lane 3: human skeletal precursor cells untreated;
Lane 4: human skeletal precursor cells treated with 10 ng/ml TGF-β1.

RNA Extraction and Semi-quantitative RT-PCR Analysis

Total RNA was extracted and DNAse-treated from human cells using the S.N.A.P.™ Kit (available from Invitrogen). One μg of total RNA was reverse-transcribed to make cDNA with oligo(dT) primer using Thermoscript (Life Technologies). Polymerase chain reaction ("PCR") was performed in a volume of 10 μl adding 1 μl out of 60 μl of the cDNA as a template, using Taq DNA polymerase (available from Eurogentech). When the sequence of the gene was known, primers were designed on different exons in order to distinguish cDNA from genomic DNA contamination. Before PCR analysis, cDNAs were equalized for the expression of the housekeeping gene β-actin. PCR for human β-actin was carried out stopping the reaction at each cycle starting from the 17th cycle in order to make sure that PCR amplification was still in the linear phase. PCR products were electrophoresed in 1% agarose gel in TBE (Tris-borate/EDTA) electrophoresis buffer, stained with ethidium bromide, visualized by UV transillumination, and analyzed by densitometry using the Image Master software (available from Pharmacia-Biotech). cDNAs were diluted according to the relative intensity of the bands. To rule out that β-actin was differentially regulated in the different samples to be compared, the same analysis was also performed for the expression of another housekeeping gene, glucose-3-phosphate dehydrogenase (GAPDH). After equalization for β-actin and GAPDH, all samples were simultaneously tested for several genes, including the ones known to be involved in chondrogenesis and cartilage maintenance. For each gene, cycling was optimized in order that amplification was still in a linear phase when PCR was stopped for all samples.

EXAMPLE 4

Determination of Skeletal Precursor Cell Phenotypic Stability Throughout Serial Passaging At each passage of the expansion procedure of example 2, skeletal precursor cells from donors of various ages were harvested for total RNA extraction and RT-PCR analysis for the expression of 40 genes, as above described. Their molecular profile stays stable throughout serial passaging up to at least 15 passages, indicating that they can be largely expanded without hampering their property of skeletal precursors.

Figure 3:
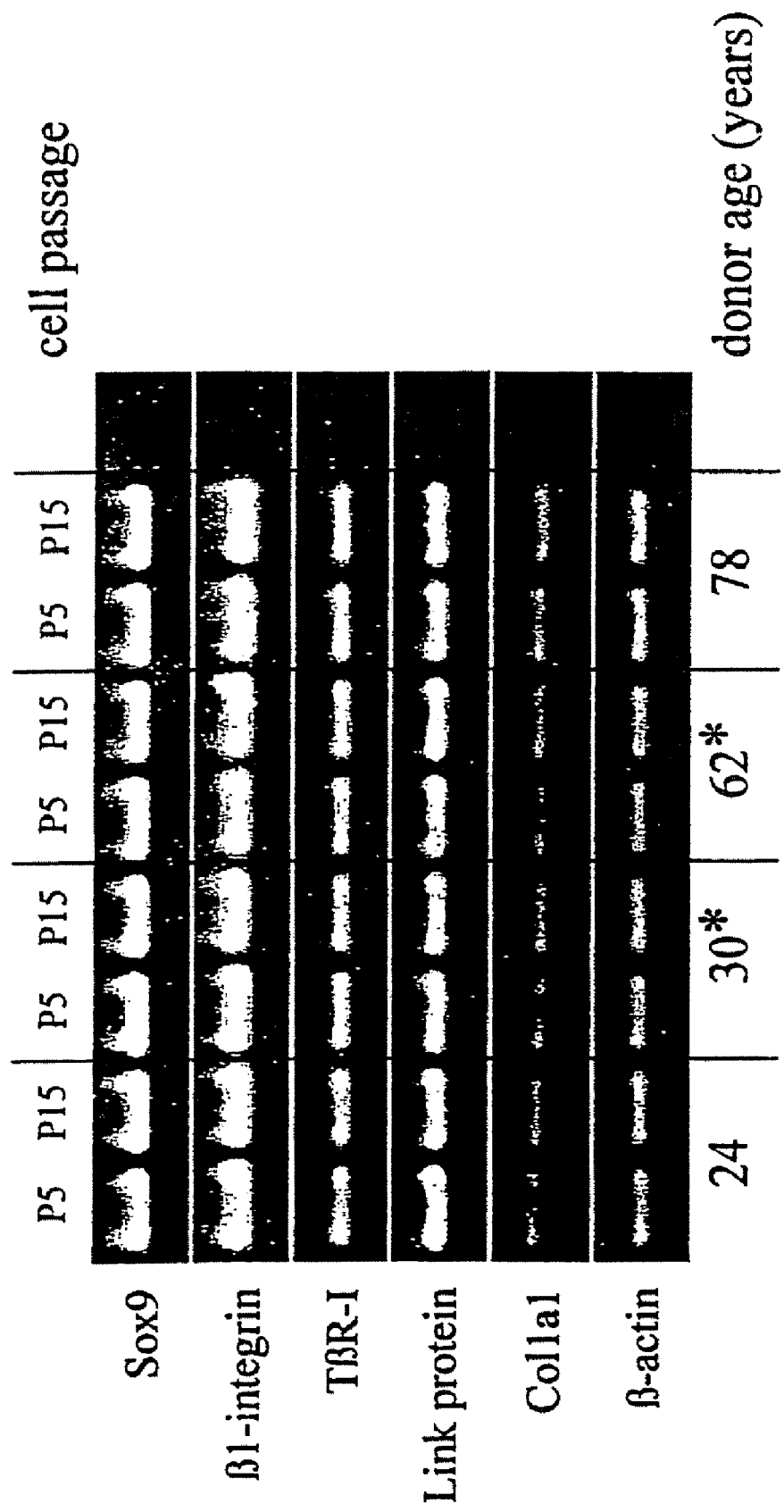
FIG. 3 shows how the phenotype of skeletal precursor cells does not depend on cell passage number or donor age. Periosteum-derived cells at P5 and P15 from four donors of different ages have a comparable molecular profile as assessed by semi-quantitative RT-PCR.

FIG. 3 shows how the phenotype of skeletal precursor cells does not depend on cell passage number or donor age. Periosteum-derived cells at P5 and P15 from four donors of different ages have a comparable molecular profile as assessed by semi-quantitative RT-PCR. The figure shows only a representative panel of the genes tested. In the last lane, Milli-Q water negative control. Templates are equalized for β-actin expression.

EXAMPLE 5

Anchorage-independent Growth of Skeletal Precursor Cells

The anchorage-independent growth of skeletal precursor cells from example 2 was assessed in vitro by agarose culture and in vivo by intramuscular injection into immunodeficient nude mice, as explained below. The injection of adult skeletal precursor cells into nude mice resulted into formation of a poorly differentiated, immature fibrocartilaginous tissue of human origin, as demonstrated by in situ hybridization for human-specific alu sequence.

Agarose Culture

Agarose culture was performed according to the method of Benya et al., *Cell* (1982) 30:215-24. Briefly, 35 mm² Petri dishes were coated with 1% sterile high $T_m$ agarose (available from Life Technologies) and placed on level surface at room temperature to solidify. Cells were released by trypsinization, counted by trypan-blue exclusion test, and resuspended in 0.5% low $T_m$ agarose (Life Technologies) in DMEM at a density of $2 \times 10^4$ cells/ml. 0.5 ml of this cell suspension was added to each of the Petri dishes. After cooling at 4° C. for 15 minutes, DMEM containing 10% FBS, antibiotics, and 50 μg/ml ascorbic acid (Sigma) was added and the Petri dishes were transferred at 37° C. in 95% humidified air and 5% $CO_2$. Medium was replaced every other day.

In Vivo Assay

Figure 4:
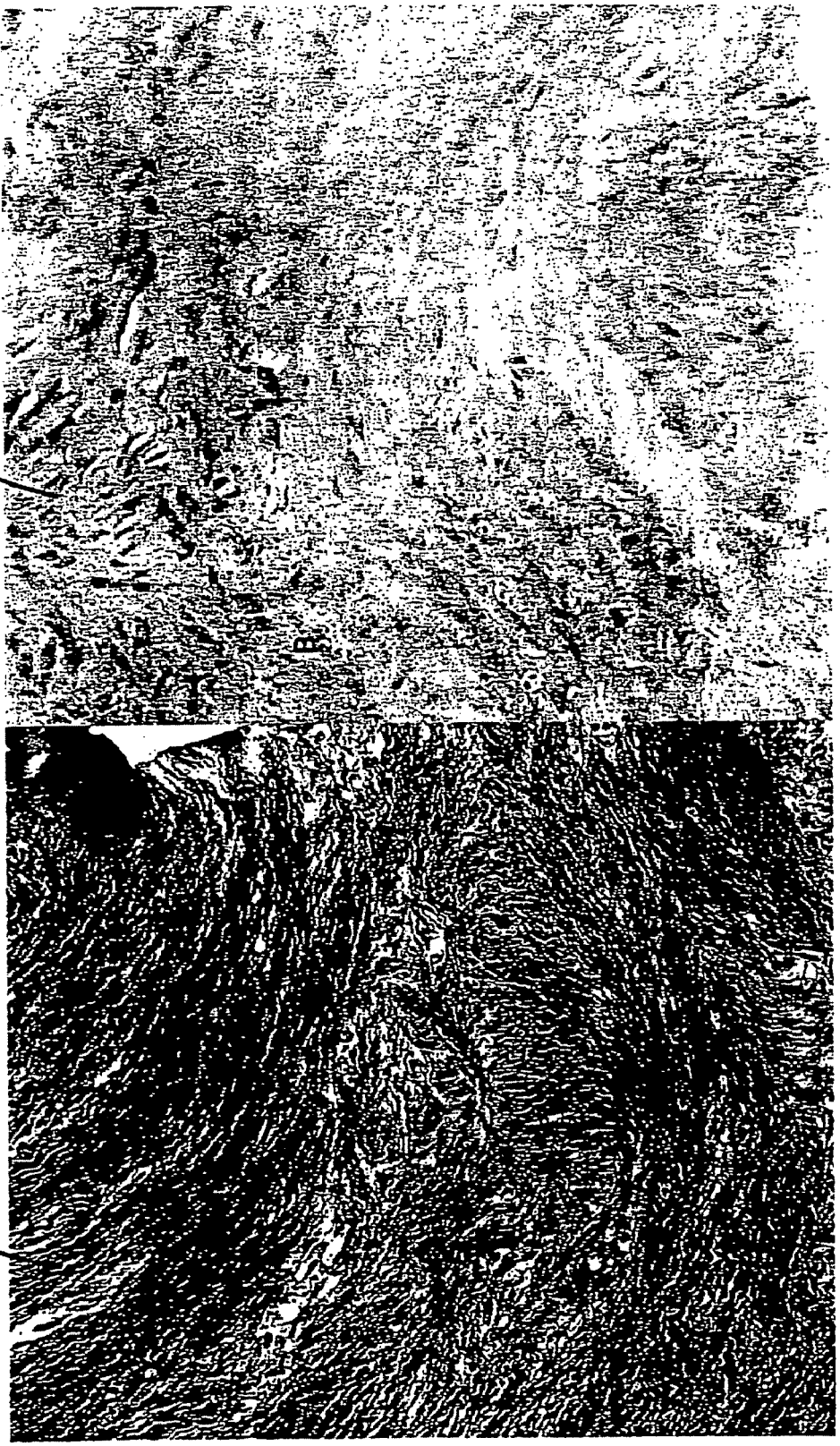
FIG. 4 consists of two histological pictures showing that skeletal precursor cells can grow anchorage-independently retaining their phenotypic stability in vivo.
Figure 5:
FIG. 5 is a picture showing that the implant retrieved from mouse muscle is formed by human cells.

Skeletal precursor cells at different passages from example 2 were released by trypsin treatment, washed twice in sterile PBS, and counted by trypan-blue exclusion test. $5 \times 10^6$ viable cells were resuspended in a volume of 50-100 μl of PBS, and injected intramuscularly in the thigh of female, 4-5 week old immunodeficient mice. Animals were sacrificed after 3 weeks by cervical dislocation and the thigh dissected to retrieve the implant. Implants were weighed, and either snap-frozen and stored in liquid nitrogen or fixed in freshly-made 4% formaldehyde for 4 hours. After fixation the samples were embedded in paraffin, sectioned at 5 μm and stained according to standard protocols (alcian blue pH 2.5, toluidine blue, Masson's trichrome, safranin O) (Manual of Histological Techniques). FIG. 4 shows implants retrieved from nude mice three weeks after intramuscular injection of $5 \times 10^6$ adult human periosteum-derived skeletal precursor cells. The Masson's trichrome (4A) and the weak alcian blue staining at pH 2.5 (4B) show a poorly differentiated fibrous tissue highly reminiscent of periosteum. This indicates that skeletal precursor cells can grow anchorage-independently in vivo, retaining their phenotypic stability.

In situ hybridization for human-specific alu sequence was carried out on the retrieved implants for the identification of human cells as follows.

In Situ Hybridization for Human-Specific alu Repeats

In situ hybridization was performed as described by Kuznetsov et al. (1997), *J. Bone Min. Res.* 12:1335-47. FIG. 4 shows that the fibrous tissue obtained from the in vivo assay is of human origin and not from the mouse host.

EXAMPLE 6

Forming Cartilage In Vitro with Skeletal Precursor Cells

Figure 6:
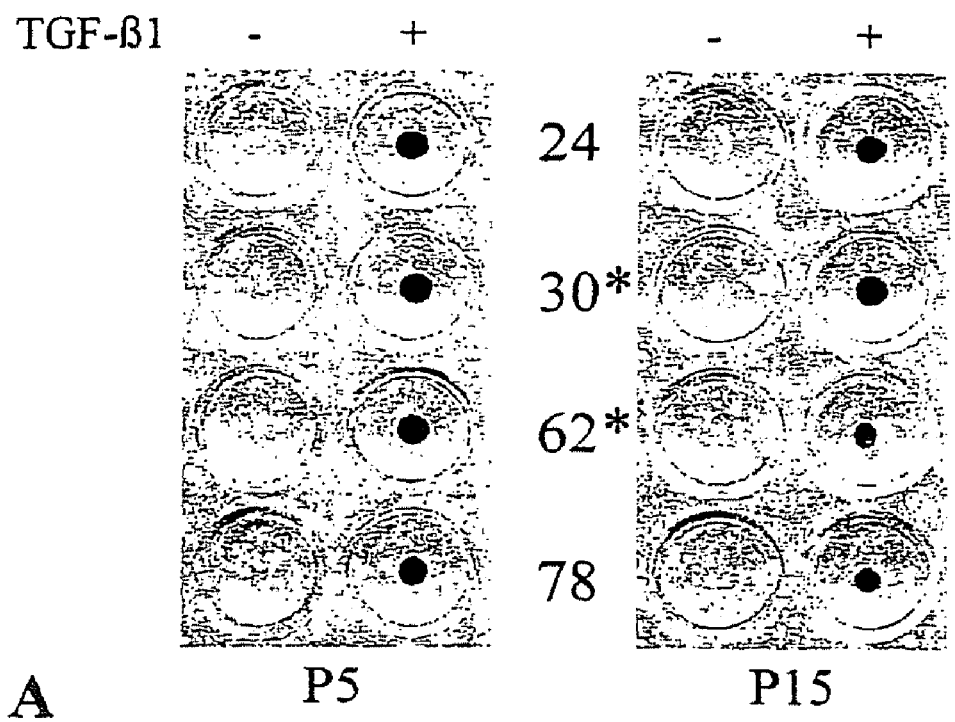
FIG. 6 consists of pictures demonstrating that chondrogenic differentiation is obtained independent of the age of the donors.
Figure 6:
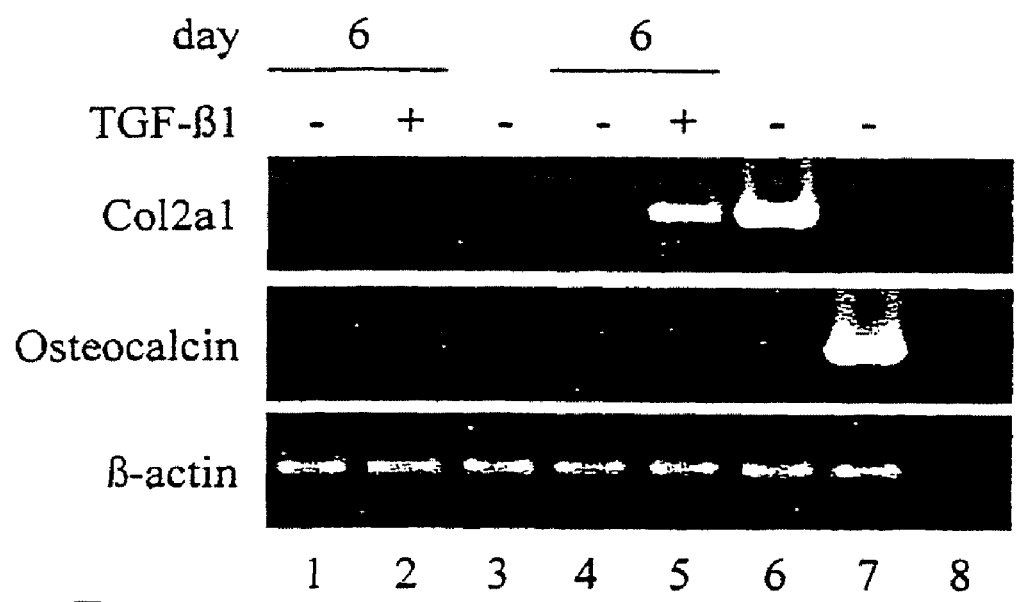

Induction and formation of cartilage in vitro, demonstrated by alcian blue staining and molecular analysis for cartilage markers by RT-PCR, was achieved by combining micromass culture of skeletal precursor cells from example 2 at a very high cell density and treatment of said cells with TGF-$\beta$ 1, or TGF-$\beta$ 2, or TGF-$\beta$ 3 (R&D systems), dissolved in 4 mM HCL containing 1 mg/ml bovine serum albumin (BSA; Serva) and added to the culture medium at a final concentration of 10 ng/ml. Chondrogenic differentiation of skeletal precursor cells was obtained in all donors, regardless of the number of cell passages or donor age, see FIGS. 6A and B. The application of TGF-$\beta$1 to skeletal precursor cells from donors aged 24, 30, 62 and 78 generated chondrocytes exhibiting collagen type 2. Under the same conditions, recombinant human bone morphogenic protein (BMP)$_2$, BMP-4 (Genetics institute), BMP-7 or GDF-5 (CDMP-1; Creative Biomolecules) dissolved in 45% acetonitrile, 0.1% trifluoroacetic acid (TFA) and added to the culture medium at final concentrations of 100-300 ng/ml, proved much less effective than TGF$\beta$s.

Micromass Culture

Expanded skeletal precursor cells from human donors of various ages at different passages from example 2 were released by trypsin treatment, counted by trypan-blue exclusion test, and resuspended in DMEM supplemented with 10% FBS and antibiotics at a cell density of $2 \times 10^7$ viable cells per ml. Micromass cultures were obtained by pipetting 20 µl-droplets of cell suspension into individual wells of 24-well plates. After cells were allowed to attach without medium for 3 hours, chemically defined serum-free medium without growth factors was added. The day of introduction into micromass culture was designated as day 0. Recombinant human TGF-$\beta$ 1, or TGF-$\beta$ 2, or TGF-$\beta$ 3 (available from R & D Systems) were dissolved in 4 mM HCl containing 1 mg/ml bovine serum albumin ("BSA") and added to the culture medium at a final concentration of 10 ng/ml every day starting on day 1, when the culture medium was changed. Same amounts of 4 mM HCl containing 1 mg/ml BSA were added to parallel cultures as controls. Micromass cultures were harvested at different periods of time for RT-PCR analysis and alcian blue staining as explained below. For comparison, human skin fibroblasts were cultured under identical conditions.

For histochemical and immunohistochemical analysis, micromass cultures were performed as described below.

Alcian Blue Staining In Vitro

Cells were rinsed twice with PBS, fixed in methanol for 1 hour at −20° C., washed with distilled water, and covered overnight with alcian blue at pH 0.2 (0.5% alcian blue 8 GS, available from Carl Roth, in 1N HCl). Quantitative analysis was performed by extracting alcian blue-stained cultures with 200 µl of 6 M guanidine HCl in Milli-Q water for 6 hours at room temperature. The optical density of the extracted dye was then measured at 630 nm using Spectronic 2000 (Bausch & Lomb). In parallel were used human skin fibroblasts as a negative control, and human articular chondrocytes as a positive control.

Figure 7:
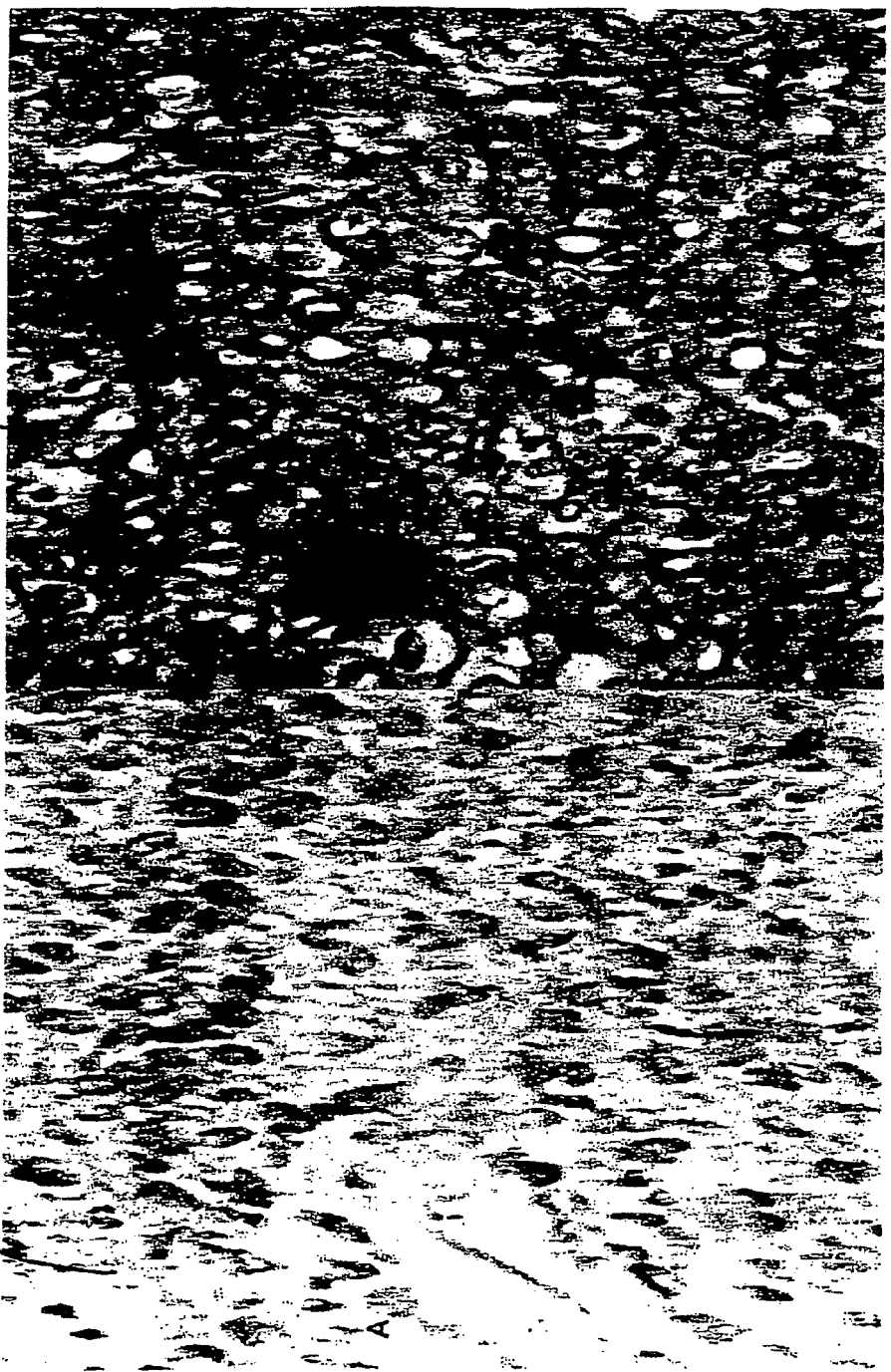
FIG. 7 shows histological pictures of cartilaginous tissue obtained in vitro from human skeletal precursor cells.

FIG. 7 shows alcian blue staining at pH 0.2 of human skeletal precursor cells in micromass culture either untreated (7A) or treated for 6 days with 10 ng/ml TGF-$\beta$1 (7B). The untreated samples show no blue colour, whereas the treated samples show strong blue staining.

Histology and Immunoistochemistry

For histological and immunohistochemical analysis, 100 µl of skeletal precursor cell suspension were plated in micromass in individual wells of a 12-well-plate. Micromasses were treated either with 10 ng/ml TGF-µ1 or with the same amount of TGF-$\beta$1 carrier solution in the chemically defined serum-free medium. After 15-20 days, micromasses were peeled off the wells, fixed with 10% formalin, embedded in paraffin, and sectioned at 5 µm. For histological evaluation, sections were deparaffinized and stained with toluidine blue, safranin 0 or alcian blue at pH 2.5 according to standard protocols (Manual of Histological Techniques). In the latter, neutral red was used for counterstaining nuclei. For immunohistochemical analysis, sections were deparaffinized and pre-digested with chondroitinase ABC (Sigma) at 50 mU/ml at room temperature for one hour to facilitate antibody access. Non-specific antibody binding was blocked by incubating the slides in 5% BSA in PBS for one hour. Sections were then incubated for one hour with a mouse anti-human type II collagen monoclonal antibody (available from Chemicon International), diluted 1:5 in 0.5% BSA in PBS. Reactivity was detected with fluorescence microscopy after incubation for one hour with a Cy3-conjugated secondary antibody (goat anti-mouse IgG; Jackson ImmunoResearch Laboratories) that had been diluted 1:500 in 0.5% BSA in PBS. Nuclei were counterstained with DAPI (4,6-diamidino-2-phenylindole; ICN).

Figure 8:
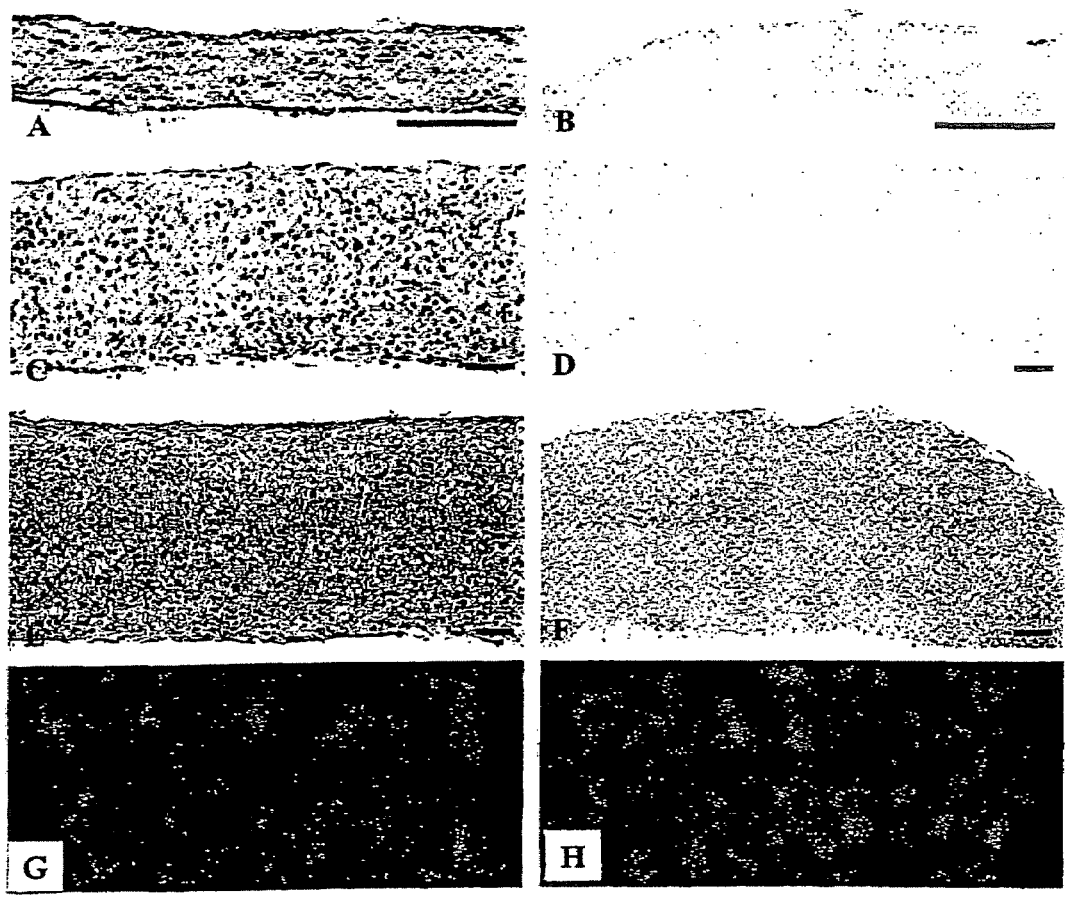
FIG. 8 A-F shows histochemical and immunohistochemical analysis of micromasses either untreated (A, B, H) or treated with TGF-$\beta$1.
Figure 9:
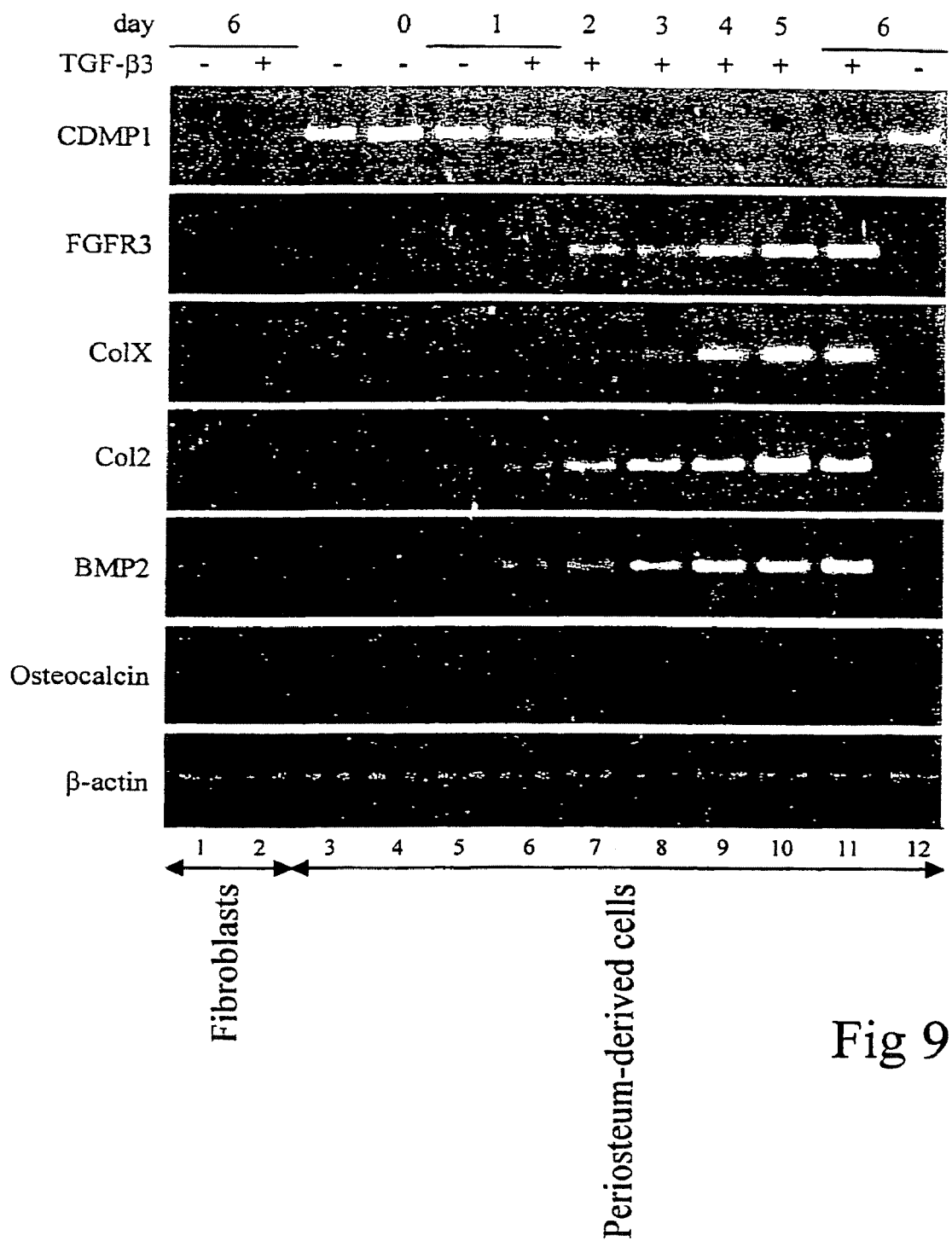
FIG. 9 shows the gene expression dynamics by RT-PCR during chodrogenesis in CDMP-1 marked skeletal precursor cells.

FIG. 8 shows histochemical and immunohistochemical analysis of micromasses either untreated (A, B, H) or treated with 10 ng/ml TGF-$\beta$1 for 15 days. CDMP-1 marked cells in micromass with TGF-$\beta$1 undergo chondrogenesis. The extracellular cartilage matrix is stained by toluidine blue (C) and alcian blue (D after 7 days, F after 15 days). The extracellular cartilage matrix is also type 2 collagen immunostained (G, H after 15 days).

EXAMPLE 7

Enhancing Cartilage Forming Ability of Chondrocytes with Skeletal Precursor Cells The interactions of skeletal precursor cells and articular chondrocytes were assessed both in vitro and in vivo. For these experiments we used human skeletal precursor cells from example 2 and pig articular chondrocytes, obtained as indicated below, in order to determine the relative contribution from the two different cell types to the cartilage forming process. As explained in example 5, the contribution of human cells can be ascertained by performing an in situ hybridization for human-specific alu genes. The addition of human skeletal precursor cells from example 3 to pig articular chondrocytes resulted in a dramatic impact on the cartilage forming potential of the chondrocytic cells. In particular, an increase in the amount of cartilage made and at the same time a decrease in the threshold of the in vivo assay (i.e. less than one million cells were required for cartilage formation and organization) were observed.

Obtaining Pig Articular Chondrocytes

Cartilage was sliced full thickness from metatarsal and metatarso-phalangeal joints from an adult pig and placed in HBSS supplemented with antibiotics. After two washes in HBSS containing antibiotics for 5 minutes at 37° C., cartilage was finely minced and placed in a sterile 0.2% crude collagenase solution in high-glucose DMEM containing 10% FBS and antibiotics. After overnight incubation at 37° C., cells were washed twice in culture medium (DMEM containing 10% FBS and antibiotics) and counted with trypan-blue exclusion test to adjust to the number of viable cells.

In Vitro Co-culture

Serially passaged human skeletal precursor cells from example 2 and freshly isolated pig articular chondrocytes were plated in micromass cultures, using conditions described in example 6, in the same well of a 12-well-plate, without adding growth factors. As controls, in one well were pipetted 2 micromasses of human skeletal precursor cells, and in another well 2 micromasses of pig articular chondrocytes. In each well the 2 micromasses were not in physical contact. The micromasses were harvested for histochemical analysis and staining protocols.

In Vivo Co-implantation

Serially passaged human skeletal precursor cells from example 2 and freshly isolated pig articular chondrocytes were intramuscularly injected into nude mice at different ratios, as indicated in table 2. As controls, human skeletal precursor cells and pig articular chondrocytes were also injected separately, using the same cell densities. Animals were sacrificed after 3 weeks by cervical dislocation. Implants were weighed, and either snap-frozen and stored in liquid nitrogen or fixed in freshly-made 4% formaldehyde for 4 hours. After fixation, the samples were embedded in paraffin, sectioned at 5 µm, and stained according to standard protocols (alcian blue pH 2.5, toluidine blue, Masson's trichrome, safranin O) (Manual of Histological Techniques). In situ hybridization for human-specific alu sequence was performed to detect and distinguish human skeletal precursor cells from pig articular chondrocytes within the implant. Results were as follows:

TABLE 2

| Chondrocytes | Skeletal precursor cells | Total No. of cells | Implant |
| --- | --- | --- | --- |
| 5 | 0 | 5 | Hyaline cartilage |
| 0 | 5 | 5 | Fibrous tissue |
| 4 | 1 | 5 | Hyaline cartilage |
| 4 | 0 | 4 | Hyaline cartilage |
| 2.5 | 2.5 | 5 | Hyaline cartilage |
| 2.5 | 0 | 2.5 | Hyaline cartilage |
| 1 | 4 | 5 | Hyaline cartilage |
| 0.5 | 4.5 | 5 | Hyaline cartilage |

All numbers of cells are expressed in millions.

FIG. 8 shows the gene expression dynamics determined by RT-PCR during chondrogenesis in CDMP-1 marked skeletal precursor cells.

Lanes 1 and 2: human dermal fibroblasts
Lane 3: human skeletal precursor cells in monolayer
Lane 4-12: human skeletal precursor cells in micromass It can be seen that CDMP1 is strongly downregulated as skeletal precursor cells enter chondrogenesis and mature to chondrocyte phenotype. The mature chondrocyte phenotype is heralded by the appearance of type II collagen, type X collagen, FGFR3 (fibroblast growth factor 3) and BMP2. A positive marker in accordance with the present invention such as the CDMP-1 marker or a marker or factor co-expressed or co-detectable with this marker, and a negative marker such as the chondrocyte markers type II collagen, type X collagen, FGFR3 and BMP2 or a marker co-expressed or co-detectable with any or all of these markers, are mutually exclusive. The skeletal precursor cells of the present invention may be identified by a positive marker such as CDMP-1 (or a marker or factor which is co-expressed or co-detectable with CDMP-1) which is not expressed at the same time as a negative marker such as FGFR3 or a another factor or marker co-expressed or co-detectable with FGFR3.

Although the present invention has been described with reference to skeletal precursor cells, the skilled person will appreciate that the present invention may be adapted to any form of tissue repair. The method to be followed is to identify the embryonic marker or markers that identify precursor cells for the specific tissue cells to be repaired, and then to select cells from the organism which exhibit the marker. The selected cells may then be expanded ex vivo/in vitro and subsequently re-implanted to repair the tissue.

The invention claimed is:

1. A method of identifying viable, expanded or passaged, committed skeletal precursor cells capable of differentiating into skeletal tissues comprising the step of:
    detecting the expression of cartilage-derived morphogenic protein-1 (CDMP-1) in an in vitro cell culture of cells obtained from human periosteum, synovial membrane or bone marrow,
    wherein the expression of CDMP-1 identifies skeletal precursor cells.

2. The method according to claim 1, wherein the expression of CDMP-1 is detected at the DNA, mRNA, cDNA or protein level and/or via the activity of a CDMP-1 promoter that is operably linked to a heterologous reporter gene.

3. The method according to claim 1, wherein the step of detecting CDMP-1 expression includes applying a binding agent for CDMP-1 to the in vitro cell culture.

4. The method according to claim 1, which further comprises detecting the absence of expression of a marker selected from the group consisting of FGFR3, type II collagen, type IX collagen, type X collagen, type XI collagen, and BMP-2.

5. A method of obtaining a homogenous culture of viable, expanded or passaged, committed skeletal precursor cells capable of differentiating into skeletal tissues comprising the steps of:
    a) detecting the expression of cartilage-derived morphogenic protein-1 (CDMP-1) in an in vitro cell culture of cells obtained from human periosteum, synovial membrane or bone marrow; and
    b) selecting or enriching CDMP-1 positive cells, thereby producing a homogenous culture of skeletal precursor cells capable of differentiating into skeletal tissue.

6. The method according to claim 5 wherein the expression of CDMP-1 is detected at the DNA, mRNA, cDNA or protein level and/or via the activity of a CDMP-1 promoter that is operably linked to a heterologous reporter gene.

7. The method according to claim 5, wherein the step of detecting CDMP-1 expression includes applying a binding agent for CDMP-1 to the in vitro cell culture.

8. The method according to claim 5, which further comprises detecting the absence of expression of a marker selected from the group consisting of FGFR3, type II collagen, type IX collagen, type X collagen, type XI collagen, and BMP-2.

* * * * *